United States Patent
Berezhnyy et al.

(10) Patent No.: US 10,179,070 B2
(45) Date of Patent: Jan. 15, 2019

(54) SYSTEMS AND METHODS FOR LASER BEAM DIRECT MEASUREMENT AND ERROR BUDGET

(71) Applicant: AMO Manufacturing USA, LLC, Santa Ana, CA (US)

(72) Inventors: Ihor Berezhnyy, Los Gatos, CA (US); Anatoly Fabrikant, Fremont, CA (US); Guangming Dai, Fremont, CA (US); Benjamin Logan, Los Gatos, CA (US); Anthony Tang, San Jose, CA (US); Henry Price, San Jose, CA (US); Stephen Calebotta, Saratoga, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 311 days.

(21) Appl. No.: 14/808,851

(22) Filed: Jul. 24, 2015

(65) Prior Publication Data

US 2016/0022492 A1    Jan. 28, 2016

Related U.S. Application Data

(60) Provisional application No. 62/029,172, filed on Jul. 25, 2014.

(51) Int. Cl.
*A61F 9/008* (2006.01)
*G01J 11/00* (2006.01)
(Continued)

(52) U.S. Cl.
CPC ...... *A61F 9/00802* (2013.01); *A61F 9/00804* (2013.01); *A61F 9/00814* (2013.01);
(Continued)

(58) Field of Classification Search
CPC ........... A61B 2018/00577; A61B 2018/00738; A61B 2018/00767; A61B 2018/00779;
(Continued)

(56) References Cited

U.S. PATENT DOCUMENTS

| 4,201,916 A | 5/1980 | Ellner |
| 4,916,319 A | 4/1990 | Telfair et al. |

(Continued)

FOREIGN PATENT DOCUMENTS

| EP | 0274205 A2 | 7/1988 | |
| JP | WO 2012114178 A2 * | 8/2012 | ............. H05G 2/008 |

OTHER PUBLICATIONS

International Search Report and Written Opinion dated Nov. 6, 2015 for International Patent Application No. PCT/US2015/042108 filed Jul. 24, 2015, 14 pages.

(Continued)

*Primary Examiner* — Boniface N Nganga
(74) *Attorney, Agent, or Firm* — Johnson & Johnson Surgical Vision, Inc.

(57) ABSTRACT

Embodiments of the present invention generally describe systems, devices, and methods for directly measuring pulse profiles during pulse delivery. In some embodiment, the pulse profiles may be measured while the pulse is delivered to ablate a material. Embodiments, may calculate ablation spot parameters based on the pulse profiles and may refine one or more subsequent laser pulses based on deviations from the calculated ablation spot parameters from desired ablation spot parameters. In some embodiments, a fluence profiler is provided. The fluence profiler may measure a pulse profile of a laser pulse from a portion of the laser pulse. The fluence profiler may utilize a UV radiation energy sensor device and a camera-based imager. The measurements from the UV radiation energy sensor device and the (Continued)

camera-based imager may be combined and scaled to provide a measured pulse profile that corresponds to the delivered pulse.

27 Claims, 16 Drawing Sheets

(51) Int. Cl.
  *G01J 1/42* (2006.01)
  *G01J 1/10* (2006.01)
  *G01J 1/58* (2006.01)
  *A61B 18/00* (2006.01)
  *A61B 18/20* (2006.01)

(52) U.S. Cl.
  CPC ............... *G01J 1/10* (2013.01); *G01J 1/429* (2013.01); *G01J 1/4228* (2013.01); *G01J 1/4257* (2013.01); *G01J 1/58* (2013.01); *G01J 11/00* (2013.01); *A61B 2018/00577* (2013.01); *A61B 2018/00684* (2013.01); *A61B 2018/00738* (2013.01); *A61B 2018/00767* (2013.01); *A61B 2018/00779* (2013.01); *A61B 2018/2035* (2013.01); *A61F 2009/00844* (2013.01); *A61F 2009/00855* (2013.01); *A61F 2009/00878* (2013.01); *A61F 2009/00882* (2013.01); *A61F 2009/00897* (2013.01)

(58) Field of Classification Search
  CPC ... A61B 2018/2035; A61F 2009/00855; A61F 2009/00844; A61F 2009/00882; A61F 9/00802; A61F 9/00814; A61F 9/00804; B23K 26/705; G01J 1/4257; G01J 2001/4261
  See application file for complete search history.

(56) References Cited

U.S. PATENT DOCUMENTS

| 5,684,566 | A | 11/1997 | Stanton | |
|---|---|---|---|---|
| 6,287,299 | B1 | 9/2001 | Sasnett et al. | |
| 6,322,555 | B1 | 11/2001 | LaHaye | |
| 2001/0056276 | A1* | 12/2001 | LaHaye | A61B 18/20 606/5 |
| 2003/0149426 | A1* | 8/2003 | Yee | A61F 9/00814 606/5 |
| 2003/0236516 | A1* | 12/2003 | Okamoto | A61F 9/008 606/5 |
| 2005/0226287 | A1* | 10/2005 | Shah | G01J 11/00 372/25 |
| 2006/0084955 | A1* | 4/2006 | Hindi | A61F 9/008 606/12 |
| 2007/0142827 | A1* | 6/2007 | Curatu | A61F 9/008 606/10 |
| 2007/0213697 | A1* | 9/2007 | Holliday | A61F 9/008 606/10 |
| 2008/0058781 | A1* | 3/2008 | Langeweyde | A61F 9/00806 606/5 |
| 2008/0186480 | A1 | 8/2008 | Lang et al. | |
| 2009/0185173 | A1 | 7/2009 | Ashdown et al. | |
| 2011/0057120 | A1 | 3/2011 | Ostendarp et al. | |
| 2014/0158892 | A1* | 6/2014 | Berezhnyy | G01J 1/0403 250/368 |

OTHER PUBLICATIONS

International Preliminary Report on Patentability mailed for International Patent Application No. PCT/US2015/042108; all pages.

* cited by examiner

Coupling of the excimer beam onto the Pyroelectric camera

SYSTEMS AND METHODS FOR LASER BEAM DIRECT MEASUREMENT AND ERROR BUDGET

CROSS-REFERENCE TO RELATED APPLICATION

The present application claims the benefit of U.S. Provisional Patent Application No. 62/029,172 filed Jul. 25, 2014, the disclosure of which is incorporated herein by reference in its entirety.

BACKGROUND OF THE INVENTION

The present invention generally relates to laser systems and more particularly to systems and methods for directly measuring a laser beam energy for uniformity, shape, size, and position of laser beam pulses. Such systems and methods may be particularly advantageous in, but not limited to, refractive surgery laser systems and methods. Some embodiments may provide real-time compensations for variations during and between treatments to achieve improved clinical outcomes.

The outcome of a refractive laser system depends on the quality of treatment algorithms and the quality of the subsystems of the laser, among other factors. Corneal ablation is performed by a sequence of UV laser pulses, applied at sequential locations all over a treatment area. Each laser pulse may deviate from the desired laser pulse in location, size, shape, and uniformity during the ablation procedure. The laser subsystems that affect the delivery of laser pulses onto the human cornea may include, eye trackers, iris registration, laser calibration, and the laser beam. The uniformity of the laser pulses, as well as the size, shape, and position of the pulses contribute to the quality of the laser beam delivery. An accurate measurement of characteristics of the laser pulses may be an important factor in the quality of the refractive surgery.

Accordingly, systems, devices, and methods that increase the predictability of the laser delivery may be beneficial in improving treatment quality.

BRIEF SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

In some embodiments, a beam splitter may be used to deliver a small fraction of a laser beam to one or several UV light sensors. The UV light sensors may be at a location that is conjugate to the treatment plane (e.g., human cornea, or the like) to monitor the laser beam intensity (or fluence level) so that the laser pulse profile, size, position as well as the uniformity can be obtained in real-time. This information may then be used as a feedback system to control the delivery of the remaining laser pulses such that spontaneous response to laser energy fluctuations or position deviations may be compensated for to achieve improved clinical outcomes.

In some aspects of the invention, a method is provided. The method may include generating a first laser pulse and delivering a portion of the first laser pulse to a beam profiler and delivering a remainder of the first laser pulse to a material. The material may be ablated at a treatment plane with the remainder of the first laser pulse to create an ablation spot. A pulse profile of the first laser pulse may be measured with the beam profiler. Ablation parameters that correspond to the ablation spot may be calculated based on the measured pulse profile. A delivery of a second laser pulse to the material may be adjusted based on the measured pulse profile of the first laser pulse.

Optionally, the material comprises a tissue of an eye. The beam profiler may include a beam splitter for directing a first part of the portion of the first laser pulse to an ultraviolet radiation energy sensor and a second part of the portion of the first laser pulse to a camera-based imager. The camera-based imager may include a UV-to-visible converter plate, an image sensor, and a lens for focusing fluorescing light from a back of the UV-to-visible converter plate onto the image sensor. Optionally, the UV radiation energy sensor may include a UV-to-visible converter plate, a light blocker positioned behind to the UV-to-visible converter plate to block UV light from hitting the detector, a conical mirror for reflecting fluorescing light from an edge of the UV-to-visible converter plate onto a detector.

In some embodiments, an ablation spot shape of the first laser pulse may be calculated by identifying a contour of the pulse profile that corresponds to an ablation fluence threshold at a location equivalent to the treatment plane. An ablation spot location of the first laser pulse may be calculated by identifying a center of mass of an area inside the contour of the pulse profile that corresponds to the ablation fluence threshold. Optionally, the ablation spot uniformity of the first laser pulse may be calculated by determining a three-dimensional surface of the area inside the contour of the pulse profile that corresponds to the ablation fluence threshold.

In some embodiments, the beam profiler may be positioned to measure the pulse profile at a plane equivalent to the treatment plane.

In some embodiments, the first laser pulse may be generated at a first voltage of a laser system and adjusting the delivery of the second laser pulse may include adjusting the first voltage of the laser system to a second voltage based on the calculated ablation parameters of the first laser pulse. The second laser pulse may be delivered at the second voltage to ablate the material.

In some embodiments, the ablation parameters of the first laser pulse may be indicative of an ablation depth that is too deep and the first voltage may be decreased to the second voltage.

In situations where the ablation parameters of the first laser pulse may be indicative of an ablation depth that is too shallow and the first voltage may be increased to the second voltage.

The measured pulse profile may include a two-dimensional distribution of energy across the beam, a pulse size, a pulse shape, and a delivery position of the first pulse.

In further aspects of the invention, another method may be provided. The method may include directing a first laser pulse toward a material according to a planned treatment table. The planned treatment table may correspond to a delivery of a single laser treatment. A portion of the first laser pulse may be delivered to a beam profiler. A remainder of the first laser pulse may be delivered to a material. The material may be ablated with the remainder of the first laser pulse. A pulse profile of the first laser pulse may be measured with the beam profiler and the portion of the first laser pulse delivered to the beam profiler. The planned treatment table may be refined based on the measured pulse profile of the first laser pulse during the delivery of the single laser treatment so as to increase an accuracy of the single laser treatment.

In some embodiments, the planned treatment table may include instructions for delivering a plurality of laser pulses. The method may further include (a) delivering a subsequent laser pulse toward the material after the first laser pulse and according to the refined planned treatment table; (b) delivering a portion of the subsequent laser pulse to a beam profiler; (c) delivering a remainder of the subsequent laser pulse to the material; (d) ablating material with the remainder of the subsequent laser pulse; (e) measuring a pulse profile of the subsequent laser pulse with the beam profiler and the portion of the subsequent laser pulse delivered to the beam profiler; (f) further refining the planned treatment table based on the measured pulse size, pulse shape, and delivery position of the subsequent laser pulse; and (g) repeating steps (a)-(f) until a last laser pulse of the plurality of laser pulses of the planned treatment table is delivered toward the material.

The method may also include calculating ablation spot parameters for each of the plurality of laser pulses delivered toward the material and summing the spot ablations to identify a total ablation profile.

Optionally, the method may include calculating a deviation of the total ablation profile from a desired ablation profile to identify a treatment error. The beam profiler may be configured to characterize the three-dimensional profile of a laser pulse using the portion of the laser pulse delivered to the beam profiler.

Refining the planned treatment table may include calculating ablation spot parameters based on the measured pulse profile and determining a deviation of calculated ablation spot parameters with expected ablation spot parameters. The expected ablation spot parameters may correspond to a desired laser pulse of the planned treatment table.

Refining the planned treatment table may include adjusting a size or location of a remaining laser pulse of the planned treatment table during the single laser treatment.

In further aspects of the invention, a system may be provided. The system may include a beam profiler for measuring laser pulse profiles and a laser system for directing a plurality of laser pulses along a beam path. A beam splitter may be positioned along the beam path to direct a portion of a laser pulse received along the beam path to the beam profiler and a remainder of the received laser pulse to ablate an eye of a patient with an ablation spot. A processor may be coupled with the laser system and the beam profiler. The processor may be configured to control a delivery of the plurality of laser pulses from the laser system based on a planned treatment table for a desired treatment and to refine the treatment table during the desired treatment based on laser pulse profiles measured by the beam profiler.

Optionally, the processor may be further configured to calculate ablation spot parameters based on the measured pulse profiles from the beam profiler.

The processor may be further configured to compare the calculated ablation spot parameters to desired ablation spot parameters corresponding to desired laser pulses of the planned treatment table. The processor may refine one or more subsequent laser pulses of the planned treatment table when there is a deviation between the calculated ablation spot parameters and the desired ablation spot parameters.

Optionally, the beam profiler may include a beam splitter for direction a first part of the portion of the received laser pulse to an ultraviolet radiation energy sensor and a second part of the portion of the received laser pulse to a camera-based imager. The camera-based imager may include a UV-to-visible converter plate, an image sensor, and a lens for focusing fluorescing light from a back of the UV-to-visible converter plate onto the image sensor. The UV radiation energy sensor may include a UV-to-visible converter plate, a light blocker positioned behind to the UV-to-visible converter plate to block UV light from hitting the detector, a conical mirror for reflecting fluorescing light from an edge of the UV-to-visible converter plate onto a detector.

The beam profiler may measure pulse profiles by associating a UV energy detected by the UV radiation energy sensor to image pixels of a beam profile captured by the camera-based imager depending on a pixel weight of the image pixels.

In further embodiments, a system may be provided that includes a processing device and a non-transitory computer-readable medium accessible by the processing device. The processing device may be configured to execute logic embodied in the non-transitory computer-readable medium and thereby perform operations including: measuring a pulse profile of a laser pulse delivered to ablate a material at a treatment plane and calculating ablation parameters of the delivered laser pulse based on the pulse profile. The calculated ablation parameters of the delivered laser pulse may be compared to desired ablation parameters. The processor may refine a subsequent laser pulse before delivery if there is a deviation between the calculated ablation parameters and the desired ablation parameters.

The processing device may further be configured to calculate ablation parameters by scaling the measured pulse profile by a size scale factor and identifying an ablation shape by identifying a contour in the scaled pulse profile that corresponds to an ablation fluence threshold at a location equivalent to the treatment plane. The processing device may determine the size scale factor by identifying a distance between two ablation spots and determining a distance between measured pulse profiles corresponding to laser pulses that ablated the two ablation spots.

The processing device may determine the ablation fluence threshold by determining a fluence magnitude of a pulse profile that corresponds to an ablation spot diameter created by the pulse profile.

The desired ablation parameters may correspond to desired laser pulses of a planned treatment table for a customized refractive laser surgery treatment.

The processing device may refine a subsequent laser pulse of the planned treatment table while the customized refractive laser surgery treatment is being delivered.

The ablation parameters may include a calculated depth of the delivered laser pulse and refining the subsequent laser pulse may be an adjustment of a voltage of the subsequent laser pulse when the calculated depth varies from a desired depth.

The invention will be better understood upon reading the following description and examining the figures which accompany it. These figures are provided by way of illustration only and are in no way limiting on the invention.

DETAILED DESCRIPTION OF THE INVENTION

Figure 1:
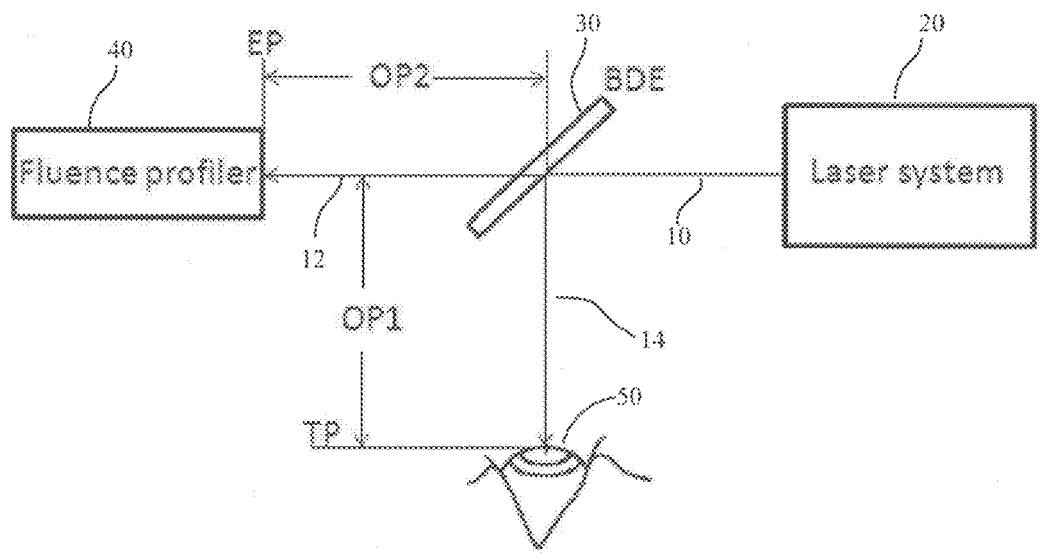
FIG. 1 illustrates an exemplary schematic of a system according to some embodiments.

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Fluence is the energy of electromagnetic radiation per unit area incident on a surface. Fluence may be used to describe the radiative energy delivered per unit area. Knowing the fluence of a laser beam may be critical for many laser applications including industrial, medical, and military. For example, in LASIK procedures, the process of ablation is initiated only when the beam fluence exceeds a fluence threshold. Accordingly, LASIK procedures generally benefit from high levels of beam homogeneity as the general uniformity of fluence across the beam provides additional outcome predictability.

Further, even if refractive lasers were subject to daily calibration to control day-to-day laser energy fluctuation and the fluence set to control the small-scale energy fluctuations between treatments, such calibration techniques may fail to provide a direct measurement and compensation for fluctuation of a laser beam within a single treatment. Accordingly, in laser ophthalmic surgery systems, in particular those in which a laser beam is used for corneal curvature modification by laser photoablation of corneal tissue, it can be useful to monitor the ablation spot at the treatment plane for controlling the laser beam, for estimating the extent of photoablation, for predicting treatment outcome, for system calibration, and others.

In a refractive surgical laser treatment, the treatment planning, the LASIK flap creation, the delivery of the laser pulses, and the ablation of these pulses onto the human cornea are considered as factors that may cause deviations from the "ideal" result.

In the treatment planning, wavefront measurement and the treatment target fitting can cause errors.

For the LASIK flap creation, the shape (circular, oval, etc.) and the uniformity may cause errors. For example, flaps created using IntraLase Femto-Second Laser that cuts LASIK flaps more uniformly compared to traditional mechanical keratome are generally associated with better clinical outcomes.

For the actual ablation of the tissue with the laser beam, humidity, plume, and tissue response may cause deviations from the "ideal" result. The humidity usually affects the ablation rate because drier corneal tissue may be cut deeper compared to a less dry cornea. Accordingly, low humidity may be associated with overcorrection. The plume may present a "shield layer" that reduces the laser beam strength and thus affect the ablation.

For the laser hardware, the uniformity, size, shape, and position of the delivered pulses may be important, as each of them may affect an outcome of a treatment. Accordingly, some embodiments are directed to a device for directly measuring laser beam parameters.

FIG. 1 illustrates an exemplary system schematic according to some embodiments. As illustrated in FIG. 1, a laser beam 10 from a laser system 20 may be sent through a beam dividing element (BDE) 30 such that a fraction 12 of the beam 10 can be sent to the fluence profiler 40 along optical path 2 (OP2). The bulk 14 of the original laser beam 10 may go through optical path 1 (OP1) to be delivered onto the patient's cornea 50.

While laser system 20 is illustrated as an ophthalmic surgery laser system it should be understood that many methods and devices disclosed herein may be applicable with other laser systems where it is desirable to measure beam energy, fluence, and profile combined or separately. As an example, the 5× Optical System from Coherent™ can be provided. This system includes in the design and configuration the beam profile monitoring at key locations throughout the optical train.

Preferably, the fraction 12 of the beam 10 that is directed to the fluence profiler does not degrade the energy for patient treatment or material ablation to a meaningful amount.

Figure 2:
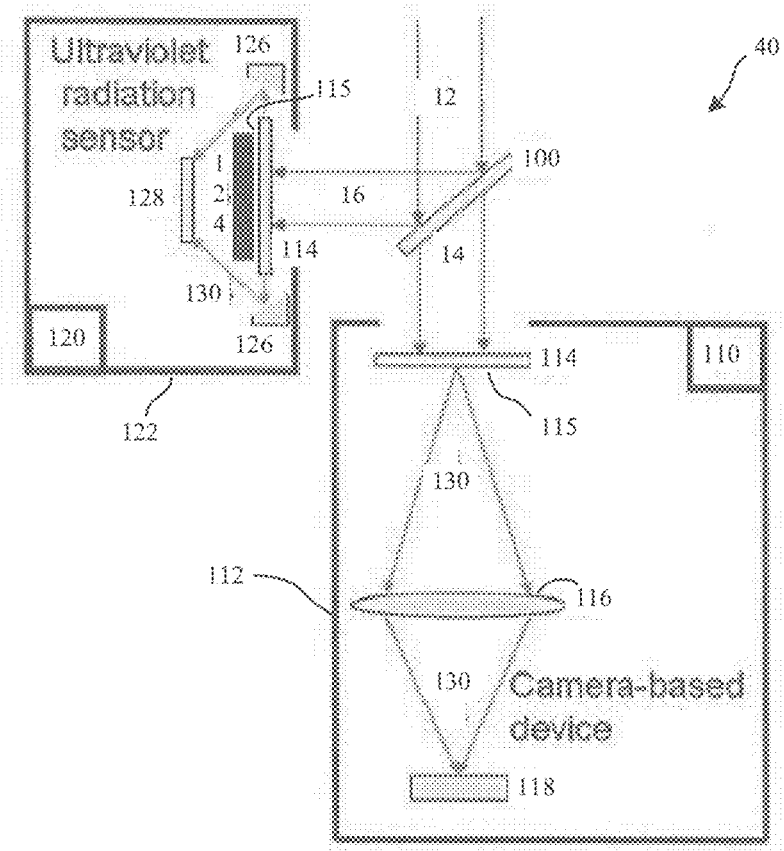
FIG. 2 illustrates an exemplary fluence profiler according to some embodiments of the invention.

FIG. 2 illustrates an exemplary fluence profiler 40 according to some embodiments of the invention. In some embodiments, fluence profiler 40 may be located at a location equivalent to the treatment plane. At this location, the fluence profile of the laser spot may be identical in shape and scaled by a magnitude to the fluence profile of the laser spot at the treatment plane. Scale factor may depend on transmission/reflection of the beam dividing element.

The exemplary UV radiation fluence profiler may work as follows. The fraction 12 of beam 10 may be split into two parts 14, 16 by beam splitter 100. The first part 14 of the fraction 12 of beam 10 may be analyzed by a camera-based device 110 and the second part 16 of the fraction 12 of beam 10 may be analyzed by an ultraviolet radiation sensor 120.

With the profile and energy measurements from the camera-based device 110 and the ultraviolet radiation sensor 120, the fluence profile may be calculated by associating the portion of the total energy to pixels of the beam profile depending on the pixel weight. Many embodiments disclosed herein may provide real-time detection of beam shape, beam size, and/or beam position. The real-time detection may be advantageous as it allows for monitoring of a treatment in real-time and if needed, revision of the treatment in real-time when deviations from a desired treatment are calculated. Further, many embodiments of the fluence profiler 40 may have little or no moving parts. And, preferably, the fluence profiler 40 may be resistant to ambient light errors when making beam size, shape, and/or position measurements, etc.

Camera-based device 110 may comprise a housing 112 for housing a UV-to-visible converter 114, an objective lens 116, and an image sensor 118. The first part 14 of the beam 10 falls on the UV-to-visible converter 114 and excites fluorescent light 130 in the visible range. Florescent light 130 propagates in all directions including directions toward the back surface 115 of the converter plate 114. The light emitted from the back surface 115 of the converter 114 is imaged by the objective lens 116 onto image sensor 118. The image sensors 118 is configured to detect the profile (shape) of florescent light that is proportional to the beam profile of the excitation UV radiation.

Ultraviolet radiation sensor 120 may comprise a housing 122 for housing a UV-to-visible converter 114, a light blocker 124, a conical mirror 126, and a detector 128. The second part 16 of the beam 10 falls on the UV-to-visible converter plate 114 and excites fluorescent light 130 in the visible range. Fluorescent light 130 propagates in all directions including directions toward the edge of the converter plate 114. Light blocker 124 may be positioned adjacent to a back surface 115 of converter plate 114 and may be configured to block ambient light from reaching detector 128. The blocker 124 may prevent light from a back surface of the UV-to-visible converter 114 from traveling past the blocker 124. The light 130 emitted from the edge of the converter plate 114 is redirected with a conical mirror 126 toward detector 128, thereby bypassing light blocker 124. The detector 128 may be configured to detect the energy of fluorescent light 130 that is proportional to the total energy of the excitation UV radiation.

While exemplary camera-based device 110 may be used for detecting the profile of florescent light, other profilers may be used. For example, the first part 14 of the beam 10 may be applied directly to an image sensor (e.g., a charge coupled device (CCD), or the like), or to a pyroelectric camera.

Figure 3:
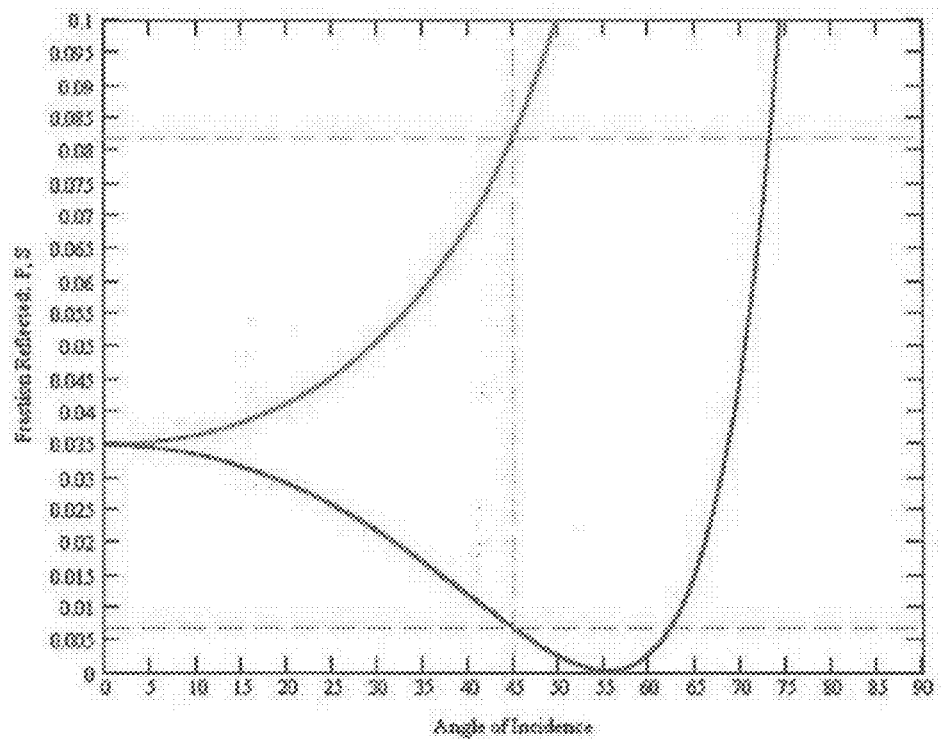
FIG. 3 illustrates reflection of S and P polarization from uncoated glass or quartz.
Figure 4:
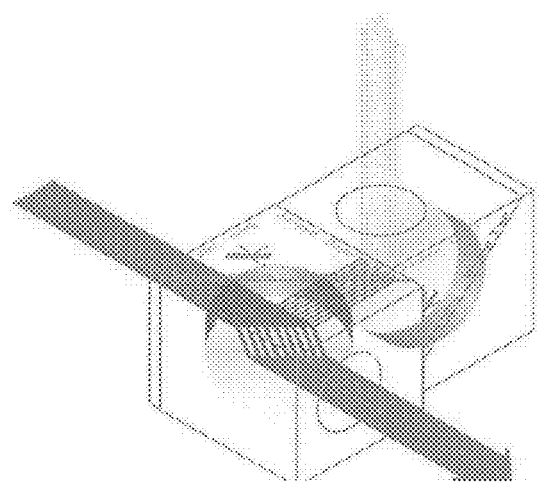
FIG. 4 illustrates an exemplary beam splitter 100 for use with some embodiments of the invention.

CCD camera sensors can detect UV beams at 355 nm, 266 nm, and 193 nm. 193 nm beams, however, may eventually damage the CCD sensor of the CCD camera. When profiling a laser by applying the beam directly to a CCD camera, the beam splitter 100 may be a quartz flat or wedge placed at 45° to the incident beam. Attenuation of the beam may occur with non-uniform reflection of S and P polarization. For example, FIG. 3 illustrates reflection of S and P polarization from uncoated glass or quartz. At 45°, the S polarization reflects at over 8% while the P polarization reflects less than 1%. To compensate for the difference in reflection, in some embodiments, the beam dividing element 30 may use two reflecting surfaces with the plane of reflection of each surface orthogonal to each other. An exemplary beam splitter 100 according to this configuration is shown in FIG. 4.

Figure 5:
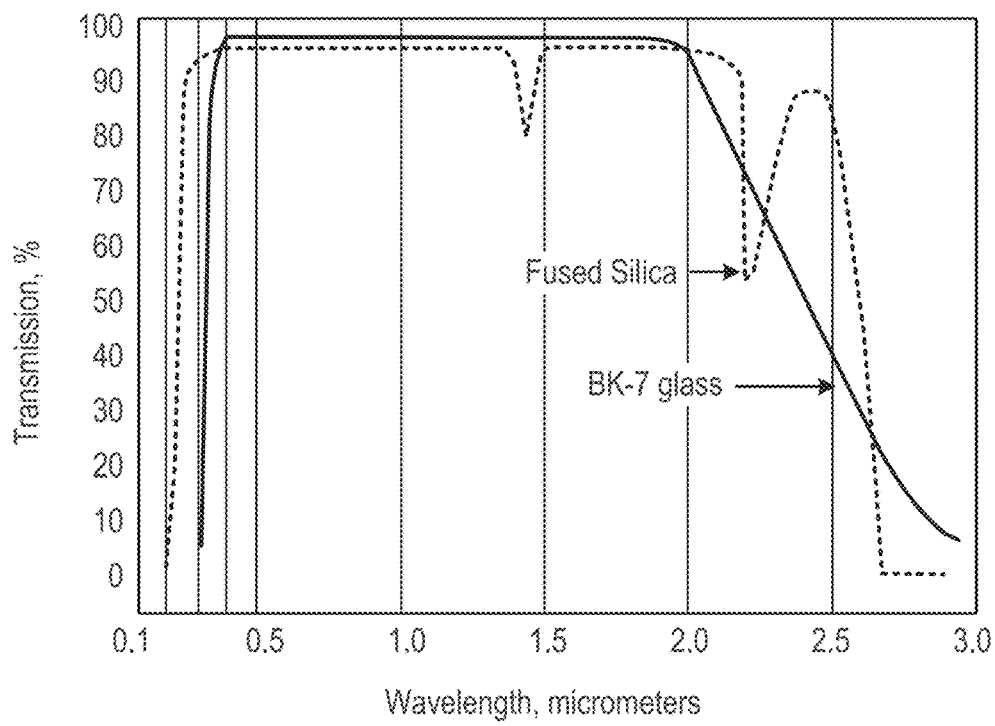
FIG. 5 illustrates the transmission of quartz (fused silica) and glass versus wavelength.
Figure 6:
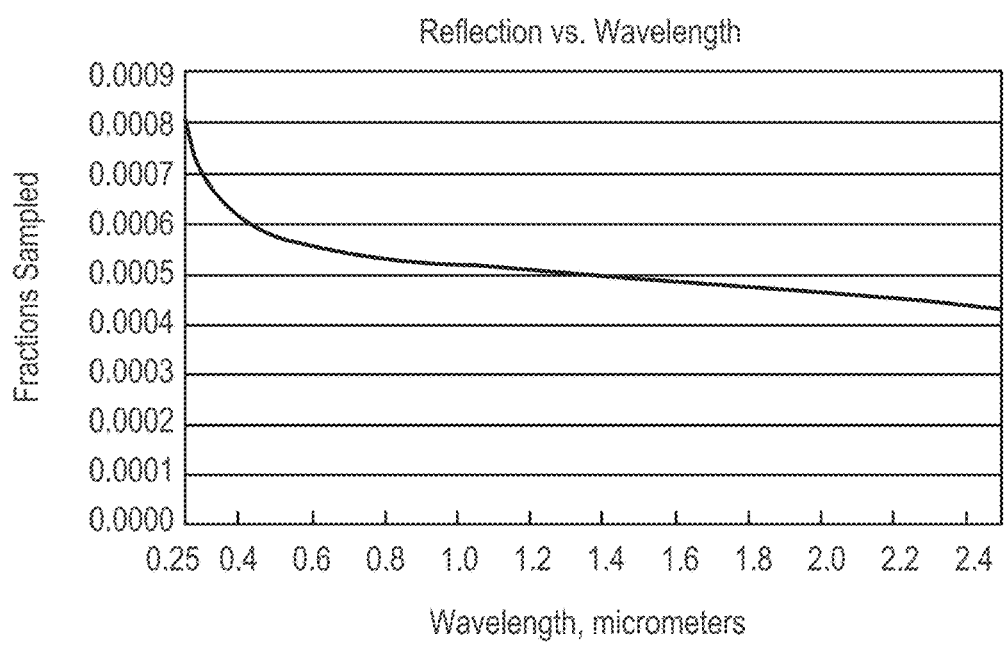
FIG. 6 illustrates the overall reflection of two surfaces of quartz versus wavelength.

Further, while quartz beam splitters may be used for many UV wavelengths, the transmission of quartz begins to fall off at 193 nm as illustrated in FIG. 5. FIG. 5 illustrates the transmission of quartz (fused silica) and glass versus wavelength. At this range, the reflection may be higher than desired as illustrated in FIG. 6. FIG. 6 illustrates the overall reflection of two surfaces of quartz versus wavelength.

Figure 7:
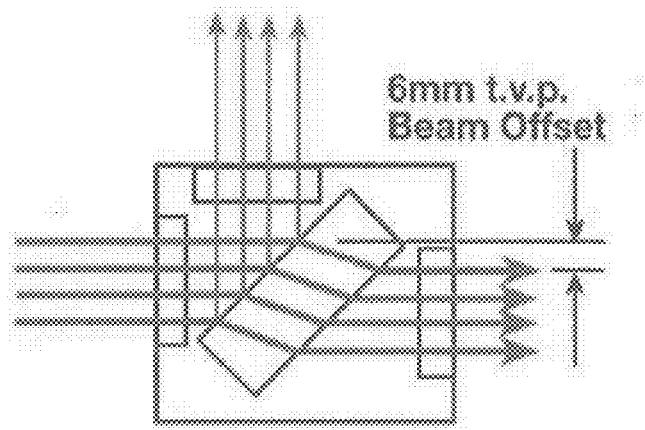
FIG. 7 illustrates an exemplary thick quartz flat used as a beam splitter for use with some embodiments of the invention.

Additionally, if the beam is reflected from both surfaces onto the camera, there may be interference fringes. One solution is to use a wedge beam splitter to separate the beams from the two surfaces. Another possibility is to use thick quartz so that the rear surface beam does not overlap with the front surface beam. FIG. 7 illustrates a thick quartz flat used as a beam splitter. This may, however, limit the size of the beam that can be reflected by the thickness of the quartz flat, as shown in FIG. 7.

Figure 8:
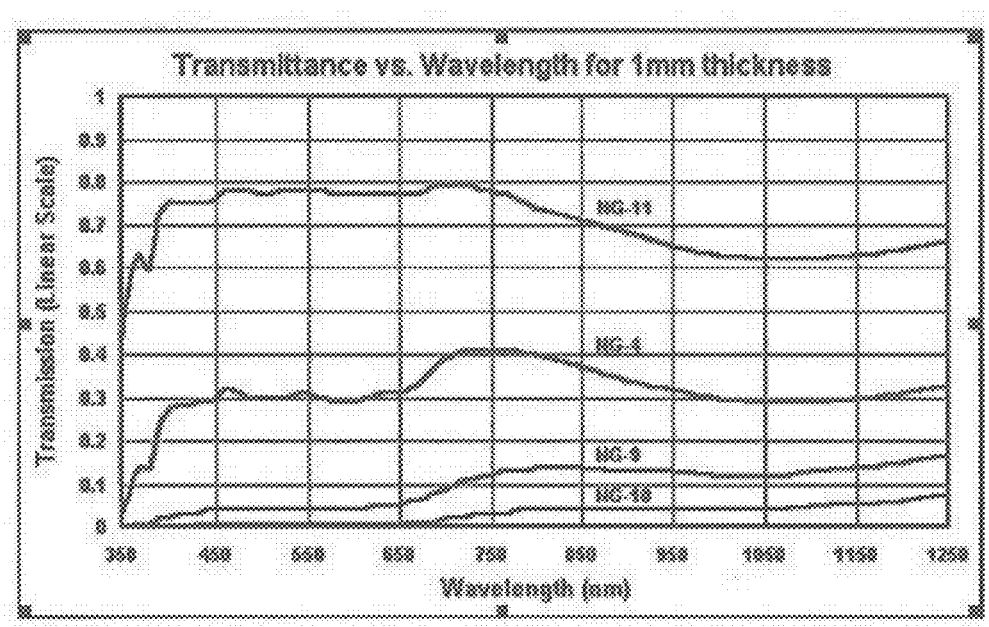
FIG. 8 provides a linear plot showing the attenuation characteristics of bulk absorbing ND filters made of glass.
Figure 9:
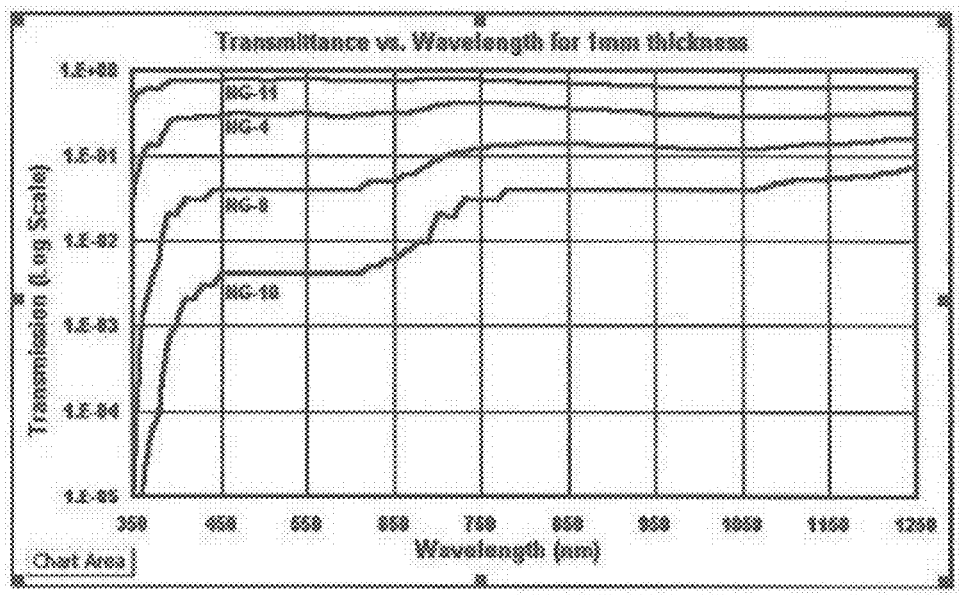
FIG. 9 provides a log plot showing the attenuation characteristics of bulk absorbing ND filters made of glass.
Figure 10:
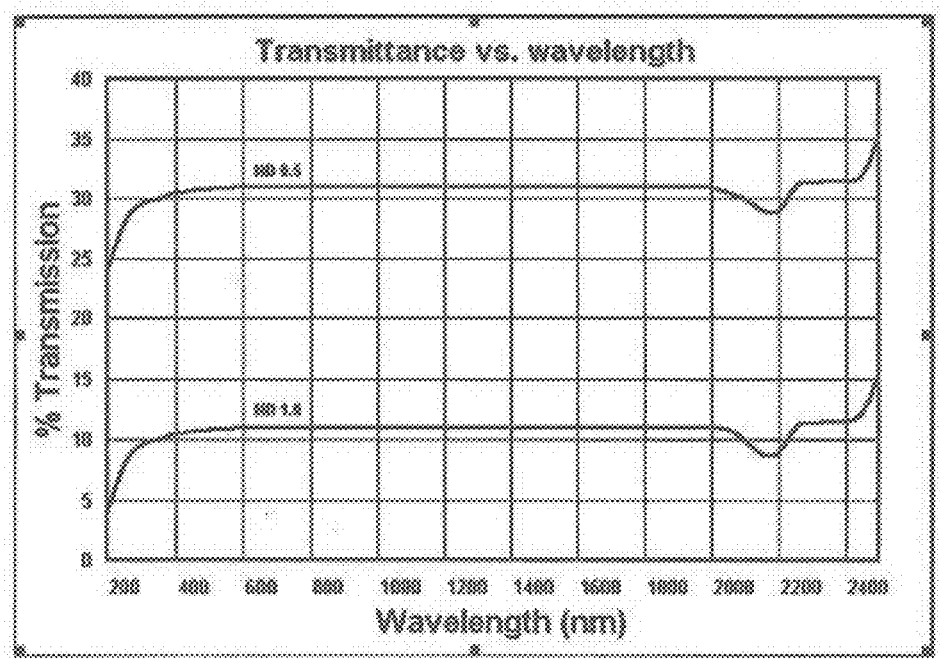
FIG. 10 shows the transmission of metalized quartz ND filters.

Additionally, ND filters may attenuate beam intensity. FIG. 8, a linear plot, and FIG. 9, a log plot, show the attenuation characteristics of bulk absorbing ND filters made of glass. While glass filters may be used in some embodiments (e.g., NG-11 for 355 nm wavelengths), incremental attenuation may be achieved using metalized quartz ND filters. FIG. 10 shows the transmission of metalized quartz ND filters. As with wedges, quartz filter transmission is falling off at 355 nm, however it may still be useful down to 193 nm as can be seen in FIG. 10. Quartz ND filters with single surface metallization may be desirable since two surface metallization may create significant interference fringes. Additionally, in some embodiments, multiple filters may be used. When multiple filters are used, it may be desirable to place the filters at angles to each other to eliminate fringes between the filters. For example, two edges, oriented similar to FIG. 4, may sufficiently reduce beam intensity for metal coated ND filters.

Figure 11:
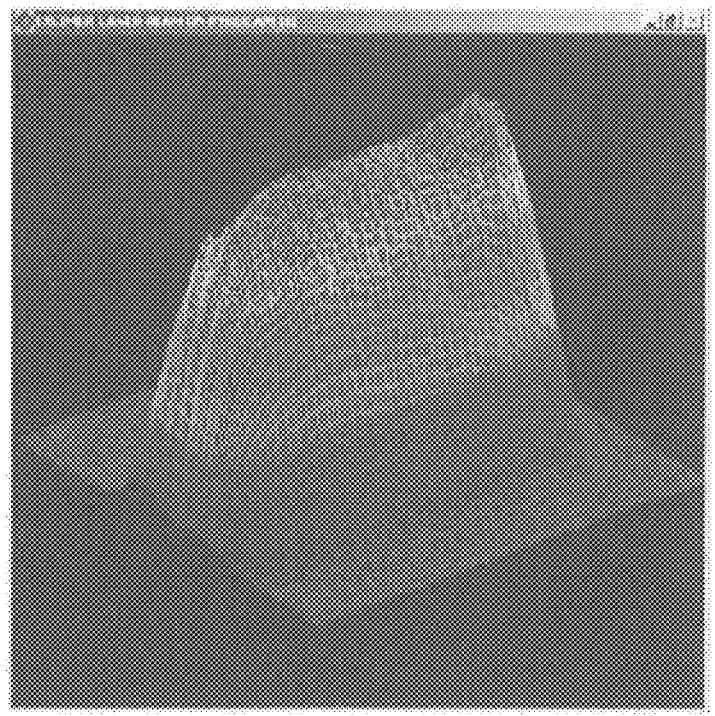
FIG. 11 shows an exemplary excimer laser beam profile as measured by a pyroelectric camera according to some embodiments of the invention.
Figure 12:
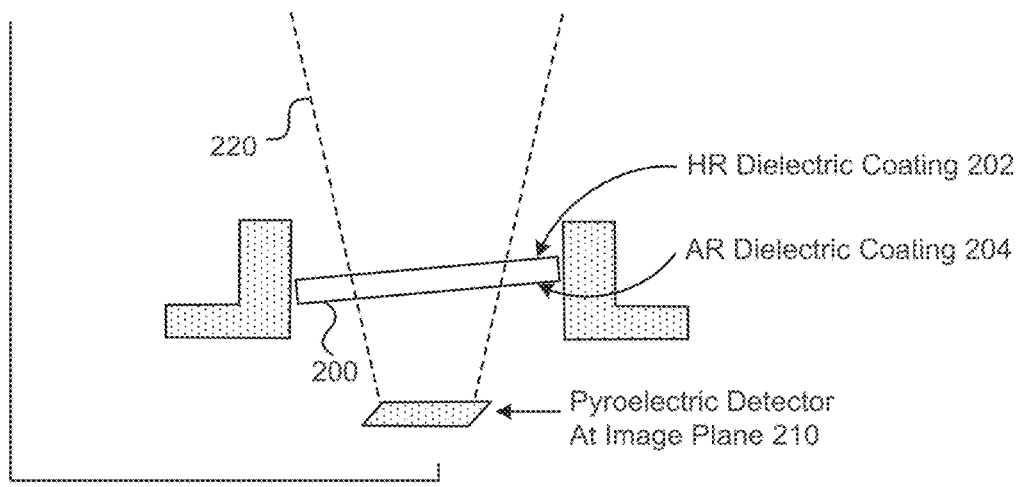
FIG. 12 illustrates an exemplary attenuation scheme for measuring excimer laser pulses with a pyroelectric camera.
Figure 13:
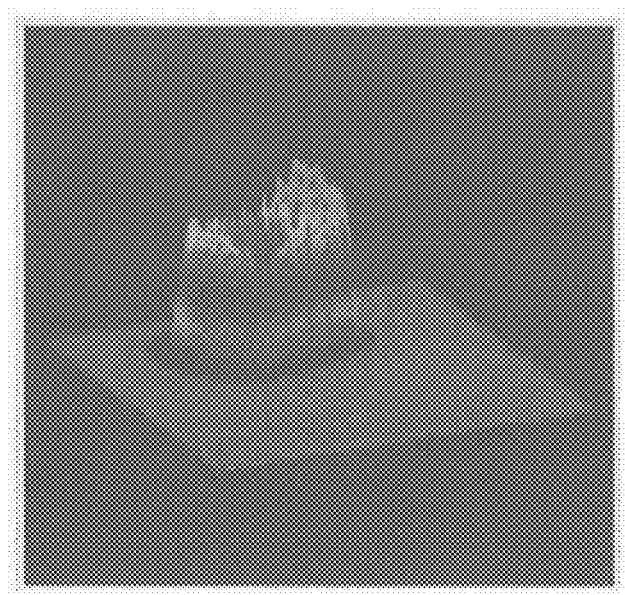
FIG. 13 shows an individual excimer laser pulse measured according to some embodiments of the invention.
Figure 14:
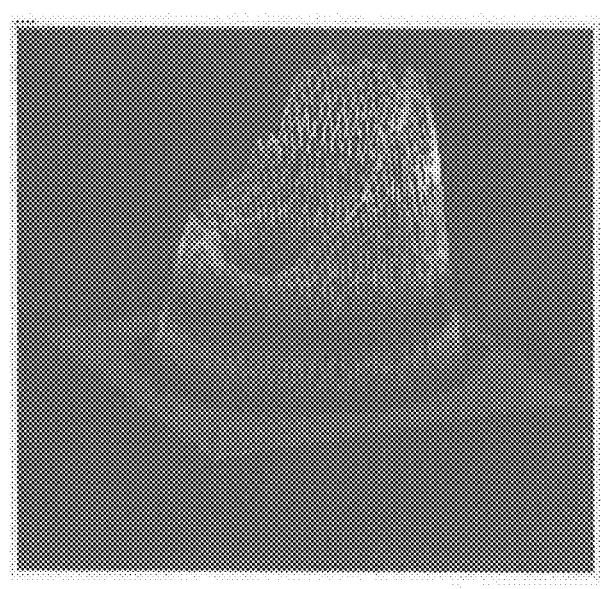
FIG. 14 shows a composite of all the pulses used in the treatment measured according to some embodiments of the invention.

As mentioned above, in some embodiments, pyroelectric cameras may be used for beam profile detection. Advantageously, pyroelectric cameras may be used in embodiments when the beams are larger than the CCD sensor of a CCD camera. For example, a typical CCD camera has an active area of less than 9 mm by 7 mm. Pyroelectric cameras on the other hand may have active areas of 12 mm by 12 mm. Additionally, pyroelectric camera sensitivity may be less than that of CCD cameras. For example, CCD cameras may saturate at about 0.3 $\mu W/cm^2$, whereas some pyroelectric cameras saturate at about 3 $W/cm^2$ (i.e., about $10^7$ more energy). Thus attenuation of the beam may be simpler with the use of pyroelectric cameras. FIG. 11 shows an exemplary excimer laser beam profile as measured by a pyroelectric camera. FIG. 12 illustrates an exemplary attenuation scheme for measuring excimer laser pulses with a pyroelectric camera. As shown in FIG. 12, a window 200 is provided in front of a pyroelectric detector 210. The laser beam 220 is focused onto the detector 210 at the image plane. The window 200 may have a front coating 202 and a back coating 204. Front coating 202 may be a high-reflector (HR) coating that reflects 99% of the UV light but passes 100% of the visible for use of alignment lasers. Back coating 204 may be an antireflective (AR) coating. With 1% transmission, the signal level is sufficient for the sensitivity of the pyroelectric camera detector 210. FIG. 13 shows an individual excimer laser pulse, and FIG. 14 shows a composite of all the pulses used in the treatment. In the example shown in FIG. 14, the composite intensity is about twice on one side as the other, illustrating the need for beam diagnostics of the laser.

Figure 15:
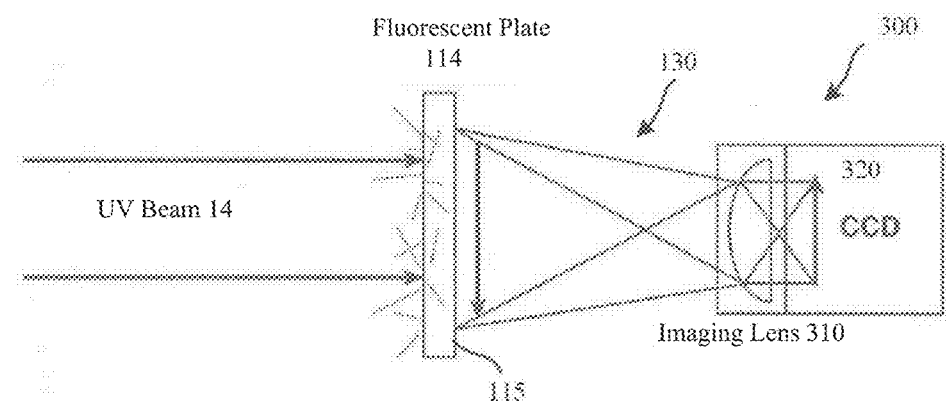
FIG. 15 illustrates a setup which may be used in camera-based devices for measuring beam profiles according to some embodiments.

While pyroelectric cameras and applying the beam directly to the CCD camera may be used to profile UV laser beams, it may be preferable to use fluorescence imaging of UV beams for profiling. The principles of fluorescence imaging are that a UV beam impinges onto fluorescing crystal. The crystal fluoresces in visible wavelengths, proportional to the UV energy in the beam. Then the visible fluorescence may be imaged with a CCD camera and a normal imaging lens. Both the crystal and the glass lens block UV scattered light so that only visible light may be imaged. A simple setup which may be used in camera-based system 110 is illustrated in FIG. 15. As illustrated, UV beam 14 may strike fluorescent plate 114. The Fluorescing/visible light 130 passes through the back surface 115 of fluorescent plate 114 and may be imaged in-line by a CCD camera 300. CCD camera 300 comprises an imaging lens 310 and a CCD sensor 320.

Figure 16:
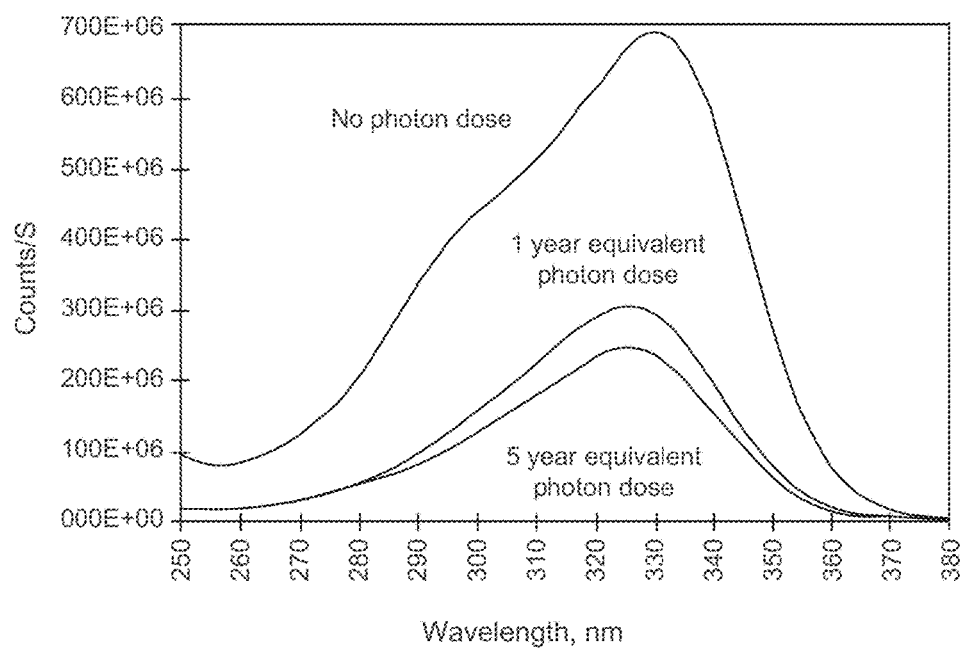
FIG. 16 shows a typical UV spectral sensitivity of Cerium doped glass.

There are many crystalline materials that fluoresce in the visible in response to UV stimulation. A typical non-crystalline material is Cerium doped glass, which may be inexpensive to use. FIG. 16 shows a typical UV spectral sensitivity of Cerium doped glass. The curves were obtained in response to the UV in sunlight. The measurement of the fluorescence was at 400 nm. As shown in FIG. 16, the visible output decreases with exposure, but eventually stabilizes.

Figure 17:
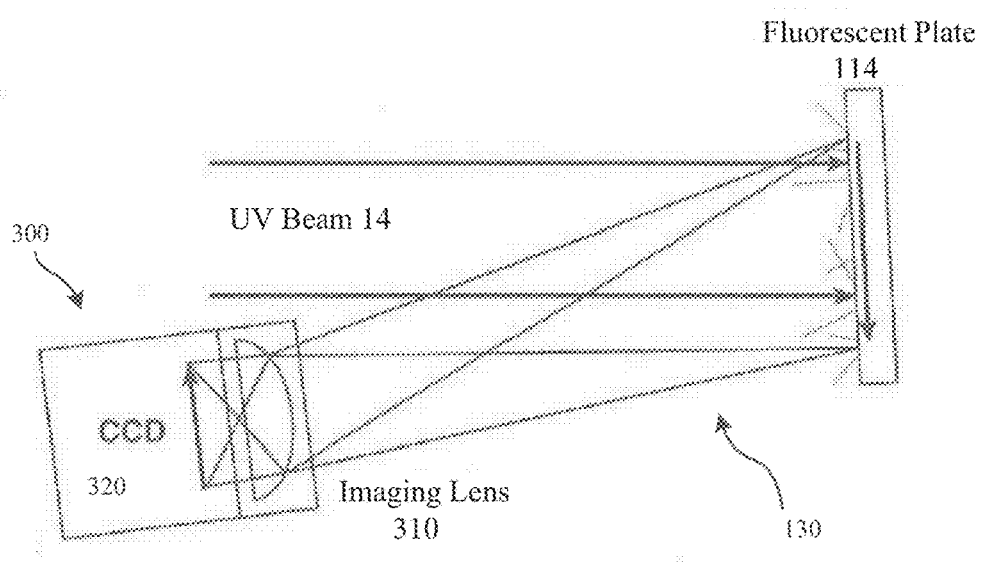
FIG. 17 illustrates another exemplary camera setup for camera-based device according to some embodiments.

FIG. 17 illustrates another exemplary camera setup for camera-based device 110. The setup of FIG. 17 provides a slightly off-axis reflection measurement where the visible light is imaged from the same side as the incident beam. As illustrated in FIG. 17, this setup may be desirable for the CCD camera 300 to be on the same side as the input beam 14. In this setup, UV input beam 14 impinges on the fluorescing plate 114. The fluorescing/visible light 130 is then imaged by the CCD camera from the front surface 117 of the fluorescing plate 114.

Figure 18:
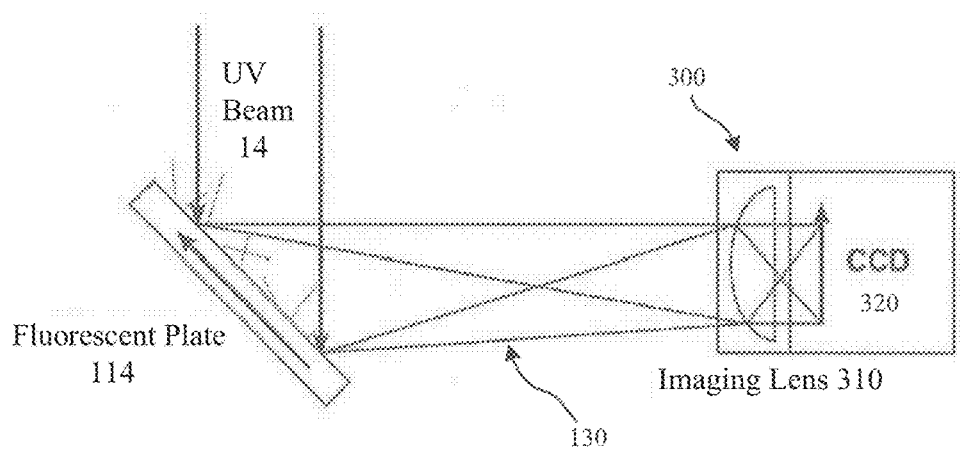
FIG. 18 illustrates yet another exemplary camera setup for camera-based device according to some embodiments.

FIG. 18 illustrates another exemplary camera setup for camera-based device 110. In the setup of FIG. 18, the fluorescing plate 114 is at 45° between the incident beam 14 and the CCD camera 300. This setup allows the CCD camera 300 to image at 90° relative to the incident beam 14.

Figures 19A, 19B:
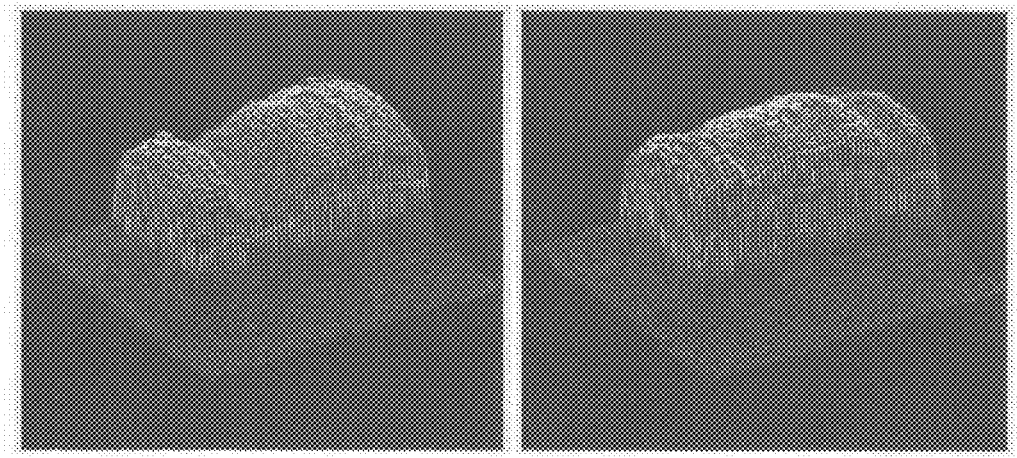
FIGS. 19A-19B provide an example of UV fluorescent imaging of a laser at 248 nm according to some embodiments of the invention before and after laser and optics tuning.

An example of UV fluorescent imaging of a laser at 248 nm is provided in FIGS. 19A-19B. A rectangular aperture was used to pick off a portion of the beam. FIG. 19A is an initial measurement and FIG. 19B is a subsequent measurement after adjustments were made to the laser and optics to provide a more uniform intensity.

UV fluorescent imaging may also be advantageous when imaging very large beams, relatively small beams, and/or beams of very high energy. The visible fluorescence may be attenuated significantly by the conversion process. Additionally, the visible light may be further attenuated with ND filters and the camera iris may provide fine incremental attenuation.

Figures 20A, 20B:
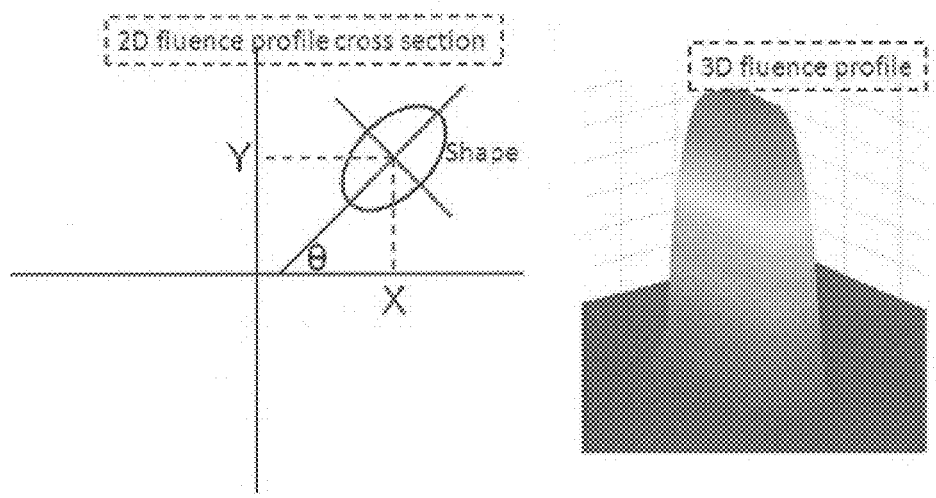
FIGS. 20A-20B illustrate a schematic of a laser pulse profile measured by a UV radiation fluence profiler according to some embodiments of the invention.

As mentioned above, with the fluence profiler 40, it is possible to characterize the three-dimensional profile of a beam pulse, which is the tissue basis data without post-surgical effects. Because the biomechanical and healing effect may be modeled in the first-order approximation as a linear scaling factor, a full characterization of the three-dimensional laser pulse profile can be useful for the calibration and revision of the current tissue and plastic basis data. FIG. 20A and FIG. 20B illustrate a schematic of a laser pulse profile measured by a UV radiation fluence profiler according to some embodiments of the invention. FIG. 20A shows a two-dimensional fluence profile cross-section. FIG. 20B shows a three-dimensional fluence profile.

After the laser spot fluence profile is obtained by a fluence profiler, the fluence profile may be processed to retrieve ablation spot parameters (e.g., shape, location, orientation, uniformity, etc.).

Figure 21:
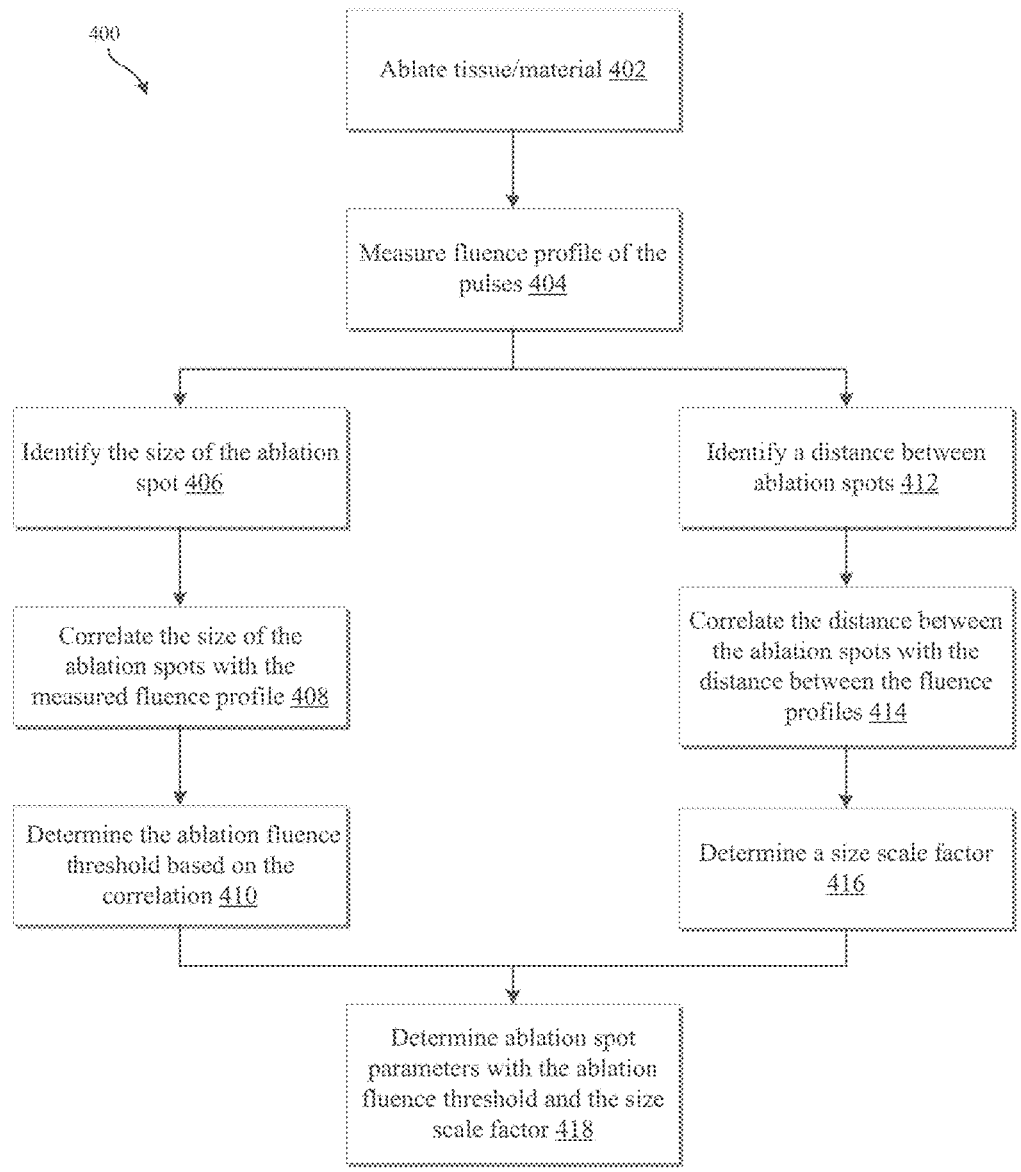
FIG. 21 illustrates an exemplary method 400 for determining an ablation fluence threshold.

FIG. 21 illustrates an exemplary method 400 for determining an ablation fluence threshold and a size scale factor for calibrating the fluence profiler for determining ablation spot parameters. At step 402, tissue/material may be ablated with one or more laser pulses. Preferably the tissue/material is ablated with two or more spots. In parallel, at step 404, the laser spot fluence profile for each pulse is recorded and digitized using a fluence profiler. To determine the ablation fluence threshold, the size of the ablation spot is determined at step 406. At step 408, the size of the ablation spot may be correlated with the measured fluence profile. The ablation fluence threshold may be determined based on this correlation, 410.

To determine a size scale factor, the tissue/material may be ablated with two or more ablation spots 402 and the fluence profile of each of these pulses are measured 404. A distance between the ablation spots may then be determined 412 (e.g., using metrological tools or the like). The distance between the ablation spots may be correlated with the distance between the fluence profiles as measured by the fluence profiler at step 414. A size scale factor may be determined based on this correlation at 416.

After the size scale factor and ablation fluence threshold are identified/calibrated, ablation spot parameters may then be determined 418.

Figure 22:
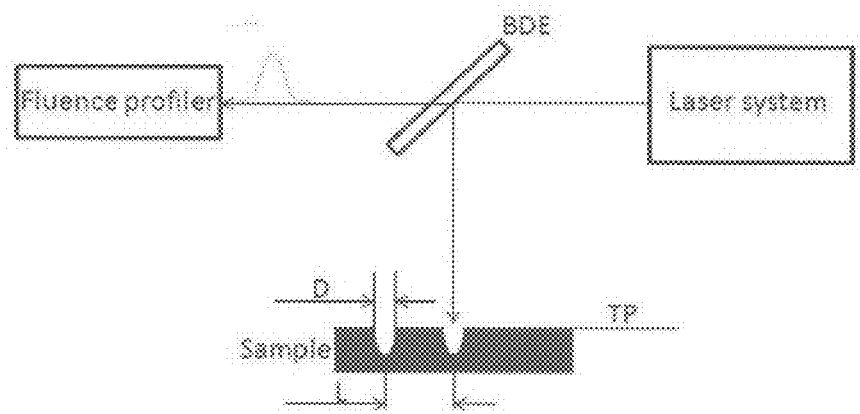
FIG. 22 illustrates the simultaneous ablation at a treatment plane TP and fluence profile detection at the equivalent plane EP.
Figure 23:
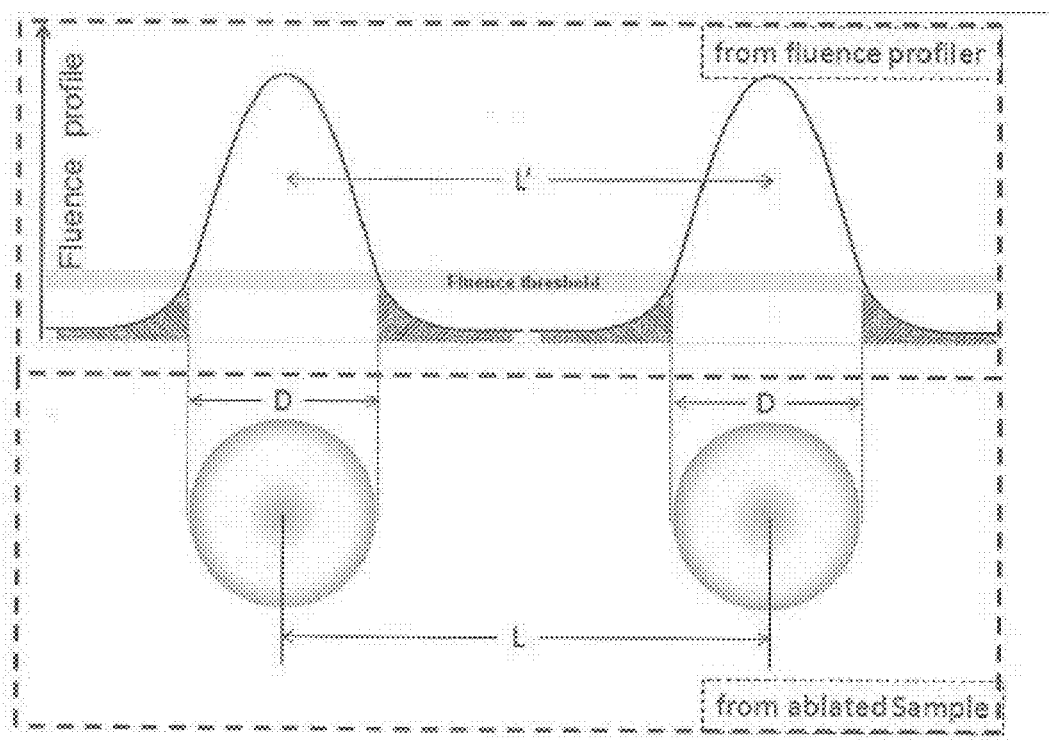
FIG. 23 exemplary fluence profiles separated by a distance L' and exemplary ablation spots with a diameter D and separated by a distance L.

FIG. 22 illustrates the ablation at a treatment plane TP and the simultaneous fluence profile detection at the equivalent plane EP. FIG. 23 illustrates exemplary fluence profiles separated by a distance L' and exemplary ablation spots with a diameter D and separated by a distance L. Preferably, the two or more spots may have a simple shape (e.g., circular, square, etc.) and separated within the fluence profiler field of view. Further, it may be beneficial to have the fluence profiler located at a location equivalent to the treatment plane (TP). Due to the equivalent location, the fluence profiler may detect the fluence profile that is identical in shape and which may be scaled by a magnitude to the fluence profile of the laser spot at the treatment plane (TP).

After the sample/tissue is ablated, the spot diameter D and the distance between spots L may be determined (e.g., using conventional metrological tools). Further, the distance L' between corresponding fluence profiles is determined by processing the data from the fluence profiler. The ratio: L/L' (size scale factor) provides a transition from a sample coordinate system to fluence profiler coordinate system and vice versa. Ablation fluence threshold may be found by determining the fluence magnitude that corresponds to the spot diameter D.

Using the determined size scale factor and ablation fluence threshold, ablation spot parameters may then be determined in real-time (e.g., throughout and during a single treatment, etc.).

For example, the ablation spot shape of subsequent beam pulses may be found by obtaining a pulse profile using the fluence profiler and then identifying a contour in the pulse profile that corresponds to the ablation fluence threshold at a location equivalent to the treatment plane.

The ablation spot location ($\bar{x}$, $\bar{y}$) may be found by calculating the first moments (center of mass) of all pixels that are located inside the contour of the fluence threshold.

$$\bar{x}(z) = \frac{\int\int_{contour} E(x, y, z) x\, dxdy}{\int\int_{contour} E(x, y, z) dxdy}.$$

$$\bar{y}(z) = \frac{\int\int_{contour} E(x, y, z) y\, dxdy}{\int\int_{contour} E(x, y, z) dxdy}.$$

Integration may be conducted over the area surrounded by the contour of the ablation fluence threshold.

The ablation spot orientation ($\varphi(z)$) may be found by initially calculating the second moments, $\sigma_x^2(z)$, $\sigma_y^2(z)$, $\sigma_{xy}^2(z)$, of all the pixels that are located inside the contour of the fluence threshold.

$$\sigma_x^2(z) = \langle x^2 \rangle = \frac{\int\int_{contour} E(x, y, z)(x - \bar{x})^2 dxdy}{\int\int_{contour} E(x, y, z) dxdy}.$$

$$\sigma_y^2(z) = \langle y^2 \rangle = \frac{\int\int_{contour} E(x, y, z)(y - \bar{y})^2 dxdy}{\int\int_{contour} E(x, y, z) dxdy}.$$

$$\sigma_{xy}^2(z) = \langle xy \rangle = \frac{\int\int_{contour} E(x, y, z)(x - \bar{x})(y - \bar{y}) dxdy}{\int\int_{contour} E(x, y, z) dxdy}.$$

Integration may be conducted over the area surrounded by the contour of the ablation fluence threshold.

After the second moments are calculated, the angle $\varphi(z)$ for ablation spot orientation may be found as:

$$\varphi(z) = \frac{1}{2}\arctan\left(\frac{2\sigma_{xy}^2}{\sigma_x^2 - \sigma_y^2}\right)$$

for $\sigma_x^2 \neq \sigma_y^2$. Otherwise, the azimuthal angle $\varphi(z)$ may be obtained by:

$$\varphi(z) = \text{sgn}(\sigma_{xy}^2)\frac{\pi}{4},$$

where:

$$\text{sgn}(\sigma_{xy}^2) = \frac{\sigma_{xy}^2}{|\sigma_{xy}^2|}.$$

The ablation spot uniformity may be found by calculating three-dimensional surface of all pixels that are located inside the contour of the ablation fluence threshold.

The above methods were validated using the fluence profiler 40 illustrated in FIG. 2. While the methods were validated using fluence profiler 40, it should be understood however, that the fluence profiler may have other configurations.

Figure 24:
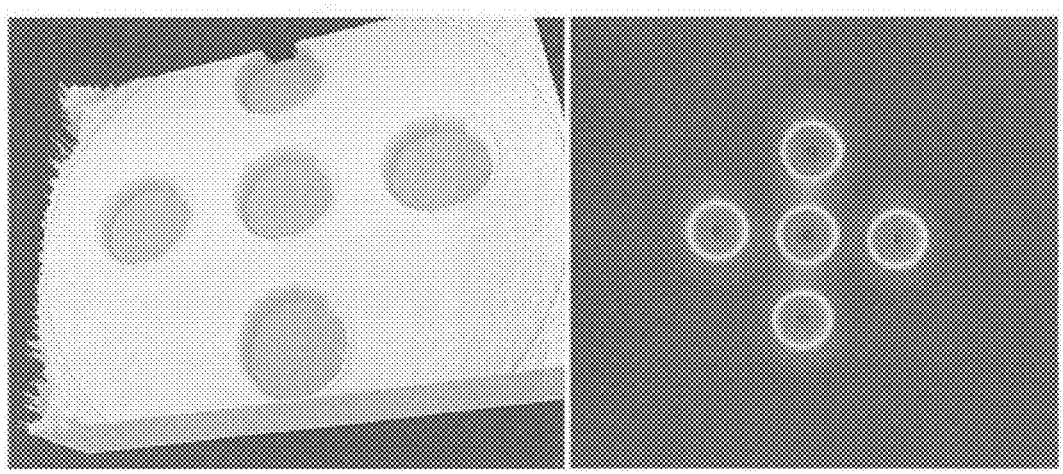
FIG. 24 demonstrates the laser spot pattern detected by the UV radiation fluence profiler simultaneously with plastic ablation.
Figure 25:
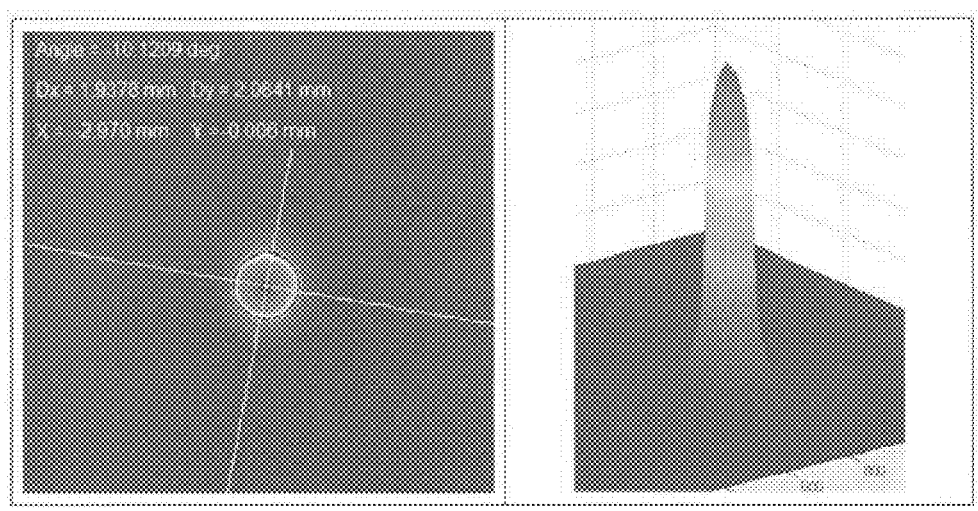
FIG. 25 shows an example of a three-dimensional pulse profile for a single pulse.

With the fluence profiler, a direct measurement of the pulse profiles can be realized. FIG. 24 demonstrates the laser spot pattern detected by the UV radiation fluence profiler simultaneously with plastic ablation. The right frame of FIG. 24 shows the laser spot two-dimensional pattern generated by indirect measurements. The left frame of FIG. 24 shows the laser spot two-dimensional pattern generated directly using the systems and methods disclosed above. FIG. 25 shows an example of a two-dimensional and a three-dimensional pulse profile for a single pulse measured using embodiments disclosed herein.

As discussed before, corneal ablation is performed by a sequence of UV laser pulses applied at sequential locations over the treatment area. Each laser pulse may deviate from design (e.g., location, size, shape, and uniformity) during the ablation. With the use of the systems, methods, and devices described herein, a direct measurement is possible for the delivered laser beam. The camera may take a picture of laser spots (sometimes of each laser spot) and perform sequential processing on the generated images.

The UV spot images may be used for several types of system error analysis. For example, a treatment may be performed and each spot image may be saved for subsequent analysis. The spot image processing may allow for the determination of the spot position and average fluence. The spot ablation can be calculated by multiplying the spot fluence by the basis function, defined for the spot size. The sum of all spot ablations gives the total ablation profile for the treatment plan. Deviation of this ablation profile from the desired ablation defines the treatment errors, which can be characterized by the root-mean-square value or by low-order and high-order aberrations. The same treatment analysis may be repeated many times and can yield the statistics of laser-related treatment errors. These errors can be used for a system error budgeting analysis to determine the priorities of fixing them.

Additionally and/or alternatively, each spot ablation may be calculated by multiplying the spot fluence profile, derived from the spot image, with the ablation depth vs. fluence function. With the use of the fluence function, the tissue ablation depth can be derived from the intensity of the spot images. Then, the sum of all spots may give the most realistic measure of the total ablation profile.

In some embodiments, the intensity distribution of each single spot can be parameterized and evaluated. For example, the spot position, intensity, uniformity, ellipticity, etc., may be calculated for single spot error analysis. Optionally, these parameters may be measured for multiple spots to provide spot parameter statistics. The purpose of this process is to determine possible shape deviations of the actual ablation from the intended shape. Such analysis may give insights as to the potential influence on the clinical outcomes, such as refractive error and high order aberrations.

Figure 26:
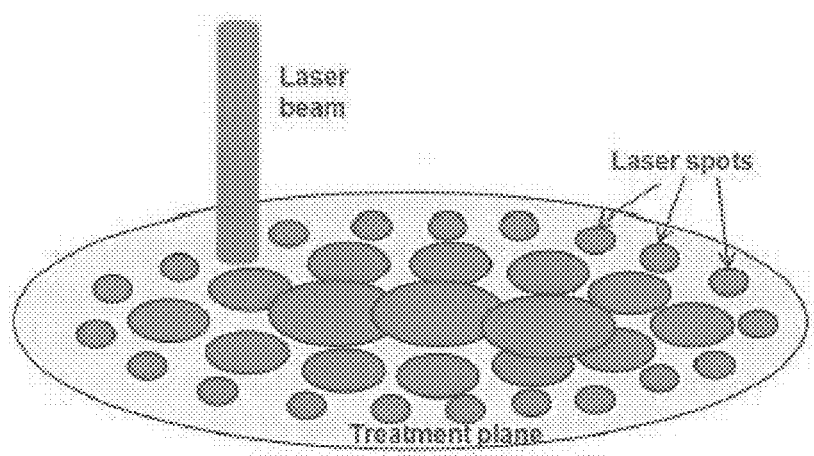
FIG. 26 illustrates an exemplary illustration of a corneal ablation treatment with sequential laser pulses with different sizes based on position.

In further embodiments, the direct fluence profile measurements may be used to calculate spatial dependence of spot parameters. The single spot statistics on the treatment periphery may be different from the single spot statistics closer to or at the center. FIG. 26 illustrates an exemplary illustration of a corneal ablation treatment with sequential laser pulses with different sizes based on position. Uniformity of the spot parameters may be an important error source. This may also be evaluated with the UV camera images. For example, if the off-center spots are skewed, say, towards the periphery like a raindrop, there would be more ablation than expected to the periphery, yielding a positive spherical aberration. Modeling such induction of spherical aberration and developing an algorithm of removing it with the system may result in improved clinical outcome, especially reduced night vision problems.

Figure 27:
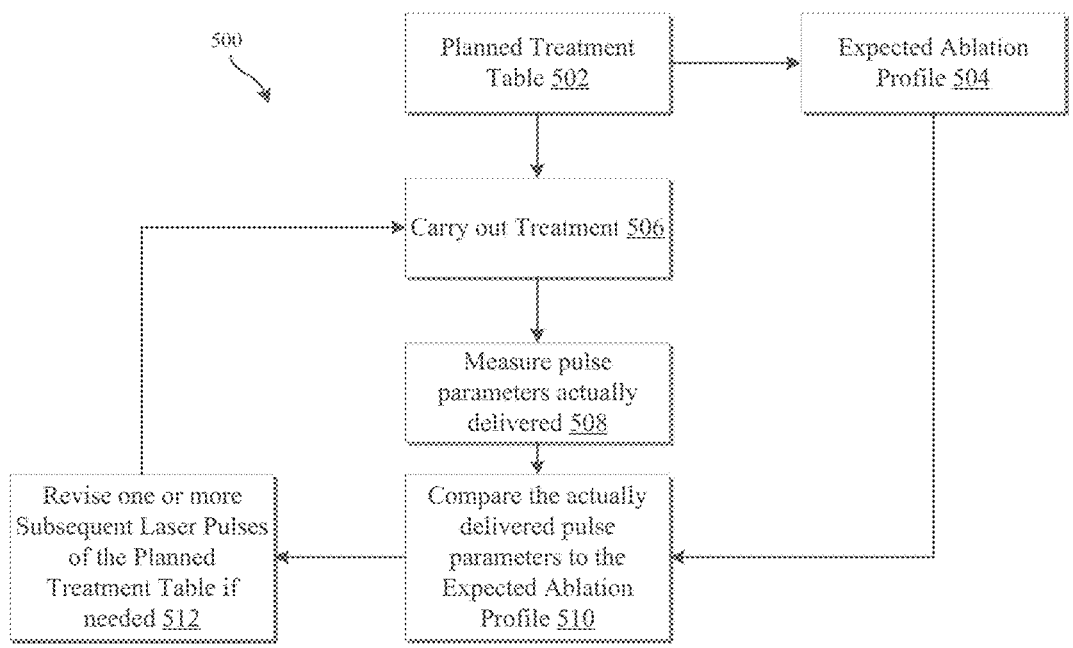
FIG. 27 illustrates an exemplary flow method 500 according to some embodiments.

In some embodiments, a real-time laser pulse controlling system and method are provided that may compensate for an deviations of pulses in terms of their shape, size, uniformity, and position of the delivery during a single refractive surgery treatment. FIG. 27 illustrates an exemplary flow method 500 according to some embodiments. A planned treatment table 502 generally comprises instructions for delivering a number of laser pulses at a pre-defined shape, size, and uniformity as well as the x-y locations. The planned treatment table 502 corresponds with an expected (or desired) ablation profile 504. The treatment may be carried out 506 according to the instructions in the planed treatment table 502. Concurrently, treatment pulse profiles may be measured with a fluence profiler during the treatment 508. The treatment pulse profiles may then be compared 510 to the expected pulse profile using a profile analyzer. If deviations are detected by the profile analyzer, real-time adjustments may be made 512 for the delivery of subsequent pulses treatment table.

For example, after the first pulse is delivered, the actual profile on the fluence profiler, which is conjugate to the corneal plane of the patient's eye, is measured and the actually delivered profile is reconstructed. The actually delivered profile may then be compared to the theoretical/desired profile from the treatment table to obtain any deviations in size, uniformity, shape, and/or location. These deviations may then be analyzed by a profile analyzer to adjust the size, and location of the remaining pulses in the treatment table. This process may be continued and the adjustment for deviations of other remaining laser pulses may be made on an on-going basis until the last laser pulse of the planned treatment is delivered. With the real-time deviation feedback system, a more accurate account of the laser pulse delivery can be expected, hence improved clinical outcome.

Figure 28:
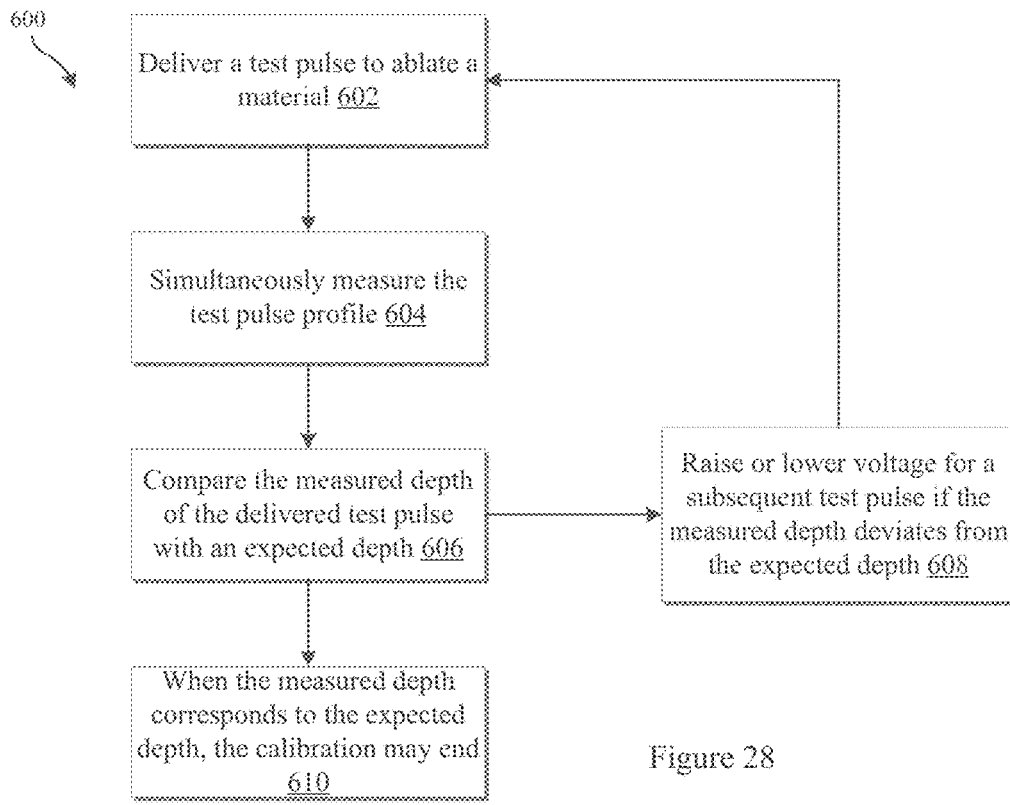
FIG. 28 illustrates an exemplary method of calibrating laser energy according to some embodiments.

Yet another use of the fluence profiler may be to calibrate the laser energy by adjusting a parameter of the laser system. For example, a voltage of the laser firing may be adjusted in real-time. FIG. 28 illustrates an exemplary method 600 of calibrating laser energy according to some embodiments. Test pulses may be delivered 602 to ablate a material. Concurrently, the test pulse profile may be measured by a fluence profiler 604 to determine a depth of the ablation. The measured depth may then be compared to the expected depth 606. If the laser pulse profile is too deep, then a decrease in voltage can be signaled to a DC box of the laser system. The DC box may then lower the voltage of the test pulse delivery. Similarly, if the pulse profile is too shallow, then an increase in voltage may be signaled to the DC box, which raises the voltage of the test pulse delivery. The process may continue until the measured depth corresponds to the expected depth within a certain threshold, thereafter the process may end 610. This process may also be implemented as a real-time control of the laser firing system such that its voltage can be controlled in real-time to maintain a consistent ablation rate of laser pulses.

Figure 29:
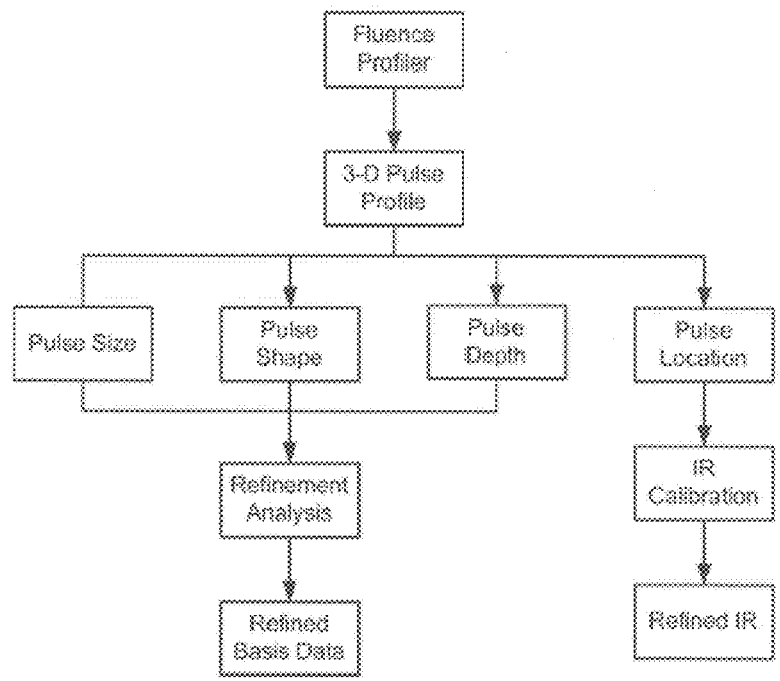
FIG. 29 illustrates an exemplary method for error budget analysis and iris registration.

Further, in some embodiments, the fluence profiler may be used for error budget analysis of the laser system. FIG. 29 illustrates an exemplary flow for error budget analysis and iris registration. For example, with a laser refractive surgery system, the fluence profiler may directly characterize the size, shape, depth, and location of laser pulses. With a refinement analysis of the size, shape, and depth of laser pulses, the human tissue basis data may be better understood. Similarly, the pulse location may be used to improve the iris registration (IR) of the laser system. With the improved basis data and IR, an improved treatment and thus better clinical outcomes may be attainable.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

Figure 30:
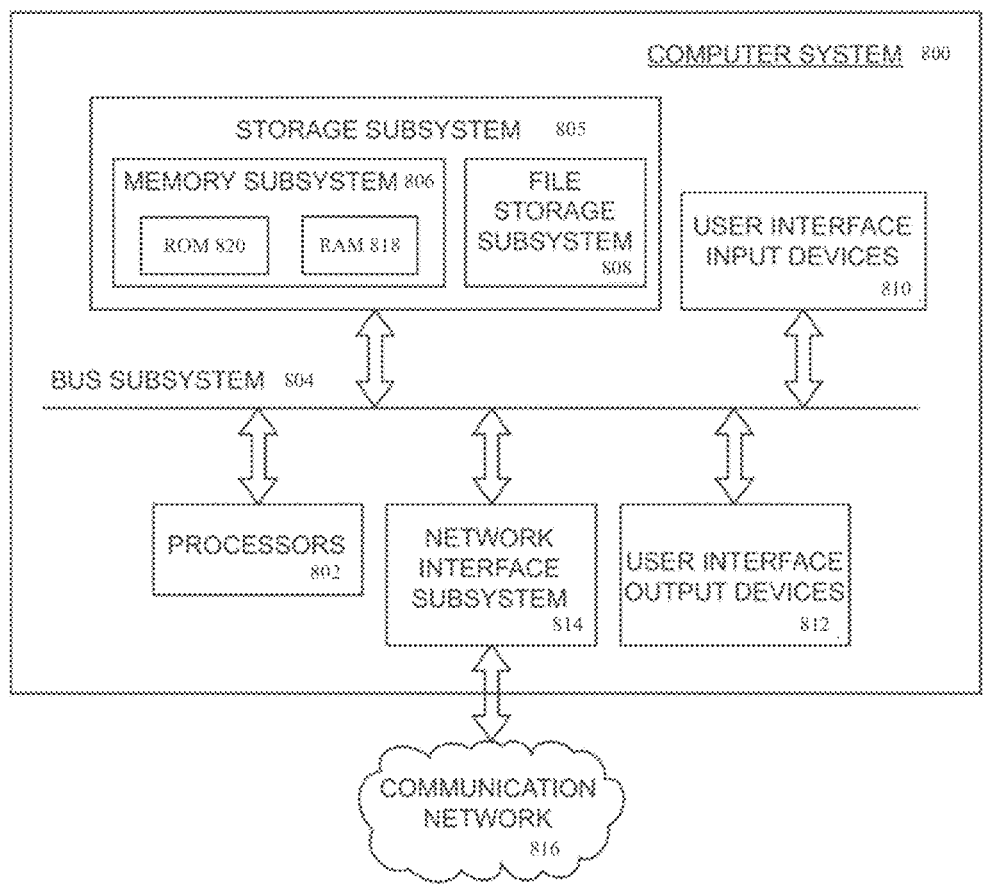
FIG. 30 illustrates an exemplary computer system that may be utilized with embodiments herein.

To this end, FIG. 30 is a simplified block diagram of an exemplary computer system 800 that may be utilized in embodiments described herein. The computer system 800 typically includes at least one processor 802 which communicates with a number of peripheral devices via a bus subsystem 804. These peripheral devices may include a storage subsystem 805, comprising a memory subsystem 806 and a file storage subsystem 808, user interface input devices 810, user interface output devices 812, and a network interface subsystem 814. Network interface subsystem 814 provides an interface to a communication network 816 for communication with other imaging devices, databases, or the like.

The processor 802 performs the operations of the computer system 800 using execution instructions stored in the memory subsystem 806 in conjunction with any data input from an operator. Such data can, for example, be input through user interface input devices 810, such as the graphical user interface. Thus, processor 802 can include an execution area into which execution instructions are loaded from memory. These execution instructions will then cause processor 802 to send commands to the computer system 800. Although described as a "processor" in this disclosure, the functions of the processor may be performed by multiple processors in one computer or distributed over several computers.

User interface input devices 810 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 812 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 805 stores the basic programming and data constructs that provide the functionality of the various embodiments. For example, database and modules implementing the functionality of embodiments described herein may be stored in storage subsystem 805. These software modules are generally executed by processor 802. In a distributed environment, the software modules may be stored in a memory of a plurality of computer systems and executed by processors of the plurality of computer systems. Storage subsystem 805 typically comprises memory subsystem 806 and file storage subsystem 808.

Memory subsystem 806 typically includes a number of memories including a main random access memory (RAM) 818 for storage of instructions and data during program execution and a read only memory (ROM) 820 in which fixed instructions are stored. File storage subsystem 68 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 808.

Bus subsystem 804 provides a mechanism for letting the various components and subsystems of the computer system communicate with each other as intended. The various subsystems and components of the computer system need not be at the same physical location but may be distributed at various locations within a distributed network. Although bus subsystem 804 is shown schematically as a single bus, alternate embodiments of the bus subsystem may utilize multiple busses.

The computer system 800 itself can be of varying types including a personal computer, a portable computer, a workstation, a computer terminal, a network computer, a module in a display unit, a mainframe, or any other data processing system. Due to the ever-changing nature of computers and networks, the description of the computer system 800 depicted in FIG. 30 is intended only as a specific example for purposes of illustrating one embodiment of the present invention. Many other configurations of the computer system are possible having more or fewer components than the computer system 800 depicted in FIG. 30.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method comprising:
   generating a first laser pulse;
   delivering a portion of the first laser pulse to a beam profiler;
   delivering a remainder of the first laser pulse to a material;
   ablating the material at a treatment plane with the remainder of the first laser pulse to create an ablation spot;
   measuring a pulse profile of the first laser pulse with the beam profiler;
   calculating ablation parameters that correspond to the ablation spot based on the measured pulse profile, the calculated ablation parameters including an ablation spot shape and an ablation spot uniformity; and
   delivering a second laser pulse to the material based on the measured pulse profile of the first laser pulse and the calculated ablation parameters;
   wherein the ablation spot shape of the first laser pulse is calculated by identifying a contour of the pulse profile that corresponds to an ablation fluence threshold at a location equivalent to the treatment plane;
wherein the ablation spot uniformity of the first laser pulse is calculated by determining a three-dimensional surface of an area inside the contour of the pulse profile that corresponds to the ablation fluence threshold.

2. The method of claim 1, wherein the material comprises a tissue of an eye, and wherein the beam profiler comprises a beam splitter for directing a first part of the portion of the first laser pulse to an ultraviolet (UV) radiation energy sensor and a second part of the portion of the first laser pulse to a camera-based imager.

3. The method of claim 2, wherein the camera-based imager comprises a UV-to-visible converter plate, an image sensor, and a lens for focusing fluorescing light from a back of the UV-to-visible converter plate onto the image sensor.

4. The method of claim 2, wherein the UV radiation energy sensor comprises a UV-to-visible converter plate, a light blocker positioned behind the UV-to-visible converter plate to block UV light from hitting a detector and a conical mirror for reflecting fluorescing light from an edge of the UV-to-visible converter plate onto the detector.

5. The method of claim 1, wherein an ablation spot location of the first laser pulse is calculated by identifying a center of mass of an area inside the contour of the pulse profile that corresponds to the ablation fluence threshold.

6. The method of claim 1, wherein the beam profiler is positioned to measure the pulse profile at a plane equivalent to the treatment plane.

7. The method of claim 1, wherein the first laser pulse is generated at a first voltage of a laser system; wherein adjusting the delivery of the second laser pulse comprises adjusting the first voltage of the laser system to a second voltage based on the calculated ablation parameters of the first laser pulse; and wherein the method further comprises delivering the second laser pulse at the second voltage to ablate the material.

8. The method of claim 7, wherein the ablation parameters of the first laser pulse are indicative of an ablation depth that is too deep and wherein adjusting the first voltage comprises decreasing the first voltage to the second voltage.

9. The method of claim 7, wherein the ablation parameters of the first laser pulse are indicative of an ablation depth that is too shallow and wherein adjusting the first voltage comprises increasing the first voltage to the second voltage.

10. The method of claim 1, wherein the measured pulse profile comprises a two-dimensional distribution of energy across the beam, a pulse size, a pulse shape, and a delivery position of the first pulse.

11. A method comprising:
directing a first laser pulse toward a material according to a planned treatment table, the planned treatment table corresponding to a delivery of a single laser treatment;
delivering a portion of the first laser pulse to a beam profiler, wherein a first part of the portion of the first laser pulse is delivered to an ultraviolet (UV) radiation energy sensor and a second part of the portion of the first laser pulse is delivered to a camera-based imager;
delivering a remainder of the first laser pulse to a material;
ablating the material with the remainder of the first laser pulse;
measuring a pulse profile of the first laser pulse with the beam profiler and the portion of the first laser pulse delivered to the beam profiler;
calculating ablation parameters based on the measured pulse profile; and
refining the planned treatment table based on the measured pulse profile of the first laser pulse and desired ablation parameters of an ablation spot during the delivery of the single laser treatment so as to increase an accuracy of the single laser treatment;
wherein the beam profiler measures pulse profiles by associating UV energy detected by the UV radiation energy sensor to image pixels of a beam profile captured by the camera-based imager depending on a pixel weight of the image pixels.

12. The method of claim 11, wherein the planned treatment table comprises instructions for delivering a plurality of laser pulses, and wherein the method further comprises:
(a) delivering a subsequent laser pulse toward the material after the first laser pulse and according to the refined planned treatment table;
(b) delivering a portion of the subsequent laser pulse to a beam profiler;
(c) delivering a remainder of the subsequent laser pulse to the material;
(d) ablating material with the remainder of the subsequent laser pulse;
(e) measuring a pulse profile of the subsequent laser pulse with the beam profiler and the portion of the subsequent laser pulse delivered to the beam profiler, wherein measuring the pulse profile includes calculating ablation parameters including a pulse size, pulse shape and delivery position of the subsequent laser pulse;
(f) further refining the planned treatment table based on the measured pulse profile including the calculated pulse size, pulse shape, and delivery position of the subsequent laser pulse and the desired ablation parameters of the ablation spot; and
(g) repeating steps (a)-(f) until a last laser pulse of the plurality of laser pulses of the planned treatment table is delivered toward the material.

13. The method of claim 12, further comprising summing spot ablations to identify a total ablation profile.

14. The method of claim 13, further comprising calculating a deviation of the total ablation profile from a desired ablation profile to identify a treatment error.

15. The method of claim 11, wherein the beam profiler is configured to characterize the three-dimensional profile of a laser pulse using the portion of the laser pulse delivered to the beam profiler.

16. The method of claim 11, wherein refining the planned treatment table comprises adjusting a size or location of a remaining laser pulse of the planned treatment table during the single laser treatment.

17. A system comprising:
a beam profiler for measuring laser pulse profiles;
a laser system for directing a plurality of laser pulses along a beam path;
a first beam splitter positioned along the beam path to direct a portion of a laser pulse received along the beam path to the beam profiler and a remainder of the received laser pulse to ablate an eye of a patient with an ablation spot; and
a processor coupled with the laser system and the beam profiler, the processor configured to control a delivery of the plurality of laser pulses from the laser system based on a planned treatment table for a desired treatment and to refine the treatment table during the desired treatment based on laser pulse profiles measured by the beam profiler;
wherein the processor is further configured to calculate ablation spot parameters based on the measured pulse profiles from the beam profiler and compare the calculated ablation spot parameters to desired ablation spot parameters corresponding to desired laser pulses of the planned treatment table;

wherein the beam profiler comprises a second beam splitter for direction a first part of the portion of the received laser pulse to an ultraviolet (UV) radiation energy sensor and a second part of the portion of the received laser pulse to a camera-based imager;

wherein the beam profiler measures pulse profiles by associating UV energy detected by the UV radiation energy sensor to image pixels of a beam profile captured by the camera-based imager depending on a pixel weight of the image pixels.

18. The system of claim 17, wherein the processor refines one or more subsequent laser pulses of the planned treatment table when there is a deviation between the calculated ablation spot parameters and the desired ablation spot parameters.

19. The system of claim 17, wherein the camera-based imager comprises a UV-to-visible converter plate, an image sensor, and a lens for focusing fluorescing light from a back of the UV-to-visible converter plate onto the image sensor.

20. The system of claim 17, wherein the UV radiation energy sensor comprises a UV-to-visible converter plate, a light blocker positioned behind the UV-to-visible converter plate to block UV light from hitting a detector and a conical mirror for reflecting fluorescing light from an edge of the UV-to-visible converter plate onto the detector.

21. A system comprising:
a processing device; and
a non-transitory computer-readable medium accessible by the processing device;
wherein the processing device is configured to execute logic embodied in the non-transitory computer-readable medium and thereby perform operations comprising:
measuring a pulse profile of a laser pulse delivered to ablate a material at a treatment plane;
calculating ablation parameters of the delivered laser pulse based on the pulse profile, the calculated ablation parameters including an ablation spot shape and an ablation spot uniformity;
comparing the calculated ablation parameters of the delivered laser pulse to desired ablation parameters of an ablation spot; and
refining a subsequent laser pulse before delivery;
wherein the ablation spot shape of the delivered laser pulse is calculated by identifying a contour of the pulse profile that corresponds to an ablation fluence threshold at a location equivalent to the treatment plane;
wherein the ablation spot uniformity of the delivered laser pulse is calculated by determining a three-dimensional surface of an area inside the contour of the pulse profile that corresponds to the ablation fluence threshold.

22. The system of claim 21, wherein the processing device calculates at least one of the ablation parameters by scaling the measured pulse profile by a size scale factor.

23. The system of claim 21, wherein the processing device determines a size scale factor by identifying a distance between two ablation spots and determining a distance between measured pulse profiles corresponding to laser pulses that ablated the two ablation spots.

24. The system of claim 21, wherein the processing device determines an ablation fluence threshold by determining a fluence magnitude of a pulse profile that corresponds to an ablation spot diameter created by the pulse profile.

25. The system of claim 21, wherein the desired ablation parameters correspond to desired laser pulses of a planned treatment table for a customized refractive laser surgery treatment.

26. The system of claim 25, wherein the processing device refines a subsequent laser pulse of the planned treatment table while the customized refractive laser surgery treatment is being delivered.

27. The system of claim 21, wherein the ablation parameters comprise a calculated depth of the delivered laser pulse and wherein refining a subsequent laser pulse comprises adjusting a voltage of the subsequent laser pulse when the calculated depth varies from a desired depth.

* * * * *